(12) United States Patent
Holton, Jr.

(10) Patent No.: US 9,629,392 B2
(45) Date of Patent: *Apr. 25, 2017

(54) TRANSLUCENT SMOKELESS TOBACCO PRODUCT

(71) Applicant: R.J. REYNOLDS TOBACCO COMPANY, Winston-Salem, NC (US)

(72) Inventor: Darrell Eugene Holton, Jr., Clemmons, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 573 days.

This patent is subject to a terminal disclaimer.

(21) Appl. No.: 13/958,228

(22) Filed: Aug. 2, 2013

(65) Prior Publication Data

US 2013/0312774 A1 Nov. 28, 2013

Related U.S. Application Data

(63) Continuation-in-part of application No. 13/614,673, filed on Sep. 13, 2012, which is a continuation-in-part of application No. 13/240,525, filed on Sep. 22, 2011, now Pat. No. 9,084,439.

(51) Int. Cl.
| | |
|---|---|
| *A24B 15/00* | (2006.01) |
| *A24B 15/24* | (2006.01) |
| *A24B 15/10* | (2006.01) |
| *A23G 3/48* | (2006.01) |
| *A24B 15/30* | (2006.01) |
| *A23G 3/54* | (2006.01) |

(52) U.S. Cl.
CPC ............... *A24B 15/24* (2013.01); *A23G 3/48* (2013.01); *A23G 3/54* (2013.01); *A24B 15/10* (2013.01); *A24B 15/245* (2013.01); *A24B 15/30* (2013.01)

(58) Field of Classification Search
CPC .... A61K 9/0056; A61K 9/0058; A24B 15/24; A24B 15/03; A24B 15/10; A24B 15/245; A24B 15/30; A23G 3/48; A23G 3/54
USPC .......................... 424/439, 440, 464; 131/359
See application file for complete search history.

(56) References Cited

U.S. PATENT DOCUMENTS

| | | |
|---|---|---|
| 2,033,909 A | 3/1936 | Cox et al. |
| 3,114,642 A | 12/1963 | Meisel |
| 3,341,414 A | 9/1967 | Cherkas et al. |
| 3,438,787 A | 4/1969 | Du Ross |
| 3,738,845 A | 6/1973 | Liebrand |
| 3,901,248 A | 8/1975 | Lichtneckert et al. |
| 4,144,895 A | 3/1979 | Fiore |
| 4,150,677 A | 4/1979 | Osborne, Jr. et al. |
| 4,267,847 A | 5/1981 | Reid |
| 4,289,147 A | 9/1981 | Wildman et al. |
| 4,351,346 A | 9/1982 | Brummer et al. |
| 4,359,059 A | 11/1982 | Brummer et al. |
| 4,452,825 A | 6/1984 | Klacik et al. |
| 4,506,682 A | 3/1985 | Muller |
| 4,589,428 A | 5/1986 | Keritsis |
| 4,605,016 A | 8/1986 | Soga et al. |
| 4,716,911 A | 1/1988 | Poulose et al. |
| 4,727,889 A | 3/1988 | Niven, Jr. et al. |
| 4,806,356 A | 2/1989 | Shaw |
| 4,887,618 A | 12/1989 | Bernasek et al. |
| 4,941,484 A | 7/1990 | Clapp et al. |
| 4,967,771 A | 11/1990 | Fagg et al. |
| 4,967,773 A | 11/1990 | Shaw |
| 4,986,286 A | 1/1991 | Roberts et al. |
| 5,005,593 A | 4/1991 | Fagg |
| 5,018,540 A | 5/1991 | Grubbs et al. |
| 5,060,669 A | 10/1991 | White et al. |
| 5,065,775 A | 11/1991 | Fagg |
| 5,074,319 A | 12/1991 | White et al. |
| 5,098,730 A | 3/1992 | Pepper et al. |
| 5,099,862 A | 3/1992 | White et al. |
| 5,110,605 A | 5/1992 | Acharya |
| 5,121,757 A | 6/1992 | White et al. |
| 5,131,414 A | 7/1992 | Fagg et al. |
| 5,131,415 A | 7/1992 | Munoz et al. |
| 5,148,819 A | 9/1992 | Fagg |
| 5,197,494 A | 3/1993 | Kramer |
| 5,230,354 A | 7/1993 | Smith et al. |

(Continued)

FOREIGN PATENT DOCUMENTS

| | | |
|---|---|---|
| EP | 2 233 134 | 9/2010 |
| KR | 2010 0117950 | 11/2010 |

(Continued)

OTHER PUBLICATIONS

Clapp, Ultrafiltration, 1990, R.J. Reynolds [online], retrieved from the Internet [retrieved Jan. 12, 2016] http://industrydocuments.libary.ucsf.edu/tobacco/docs/yuwv0095.
Product Sheet: Sugar Alcohol Liquid Malitol, Alibaba [online] retrieved from the Internet [retrieved Jan. 12, 2016] http://www.alibaba.com/product-detail/sugar-Alcohol-liquid-Maltitol_60286213186.html?spm=a2700.7724857.29.61.pHjcXi.
Geiss, V., Membrane Filtration, 1996, Viceroy[online], retrieved from Internet, [retrieved Aug. 11, 2016] https://www.industrydocumentslibrary.ucsf.edu/tobacco/docs/gpgy0147.

*Primary Examiner* — Michael H Wilson
*Assistant Examiner* — Yana B Krinker
(74) *Attorney, Agent, or Firm* — Womble Carlyle Sandridge & Rice, LLP

(57) ABSTRACT

A smokeless tobacco product is provided that includes a tobacco material in the form of a tobacco extract, a particulate tobacco material, or a combination thereof. In some embodiments, the smokeless tobacco product is substantially translucent. Methods for making and using the smokeless tobacco product are also provided. The smokeless tobacco product can include isomalt, maltitol syrup, particulate tobacco, and a translucent tobacco extract prepared by ultrafiltration.

20 Claims, 2 Drawing Sheets

(56) References Cited

U.S. PATENT DOCUMENTS

| | | |
|---|---|---|
| 5,234,008 A | 8/1993 | Fagg |
| 5,243,999 A | 9/1993 | Smith |
| 5,301,694 A | 4/1994 | Raymond et al. |
| 5,314,701 A | 5/1994 | Mentink et al. |
| 5,318,050 A | 6/1994 | Gonzalez-Parra et al. |
| 5,343,879 A | 9/1994 | Teague |
| 5,360,022 A | 11/1994 | Newton et al. |
| 5,362,496 A | 11/1994 | Baker et al. |
| 5,435,325 A | 7/1995 | Clapp et al. |
| 5,445,169 A | 8/1995 | Brinkley et al. |
| 5,512,306 A | 4/1996 | Carlsson et al. |
| 5,525,351 A | 6/1996 | Dam |
| 5,549,906 A | 8/1996 | Santus |
| 5,593,684 A | 1/1997 | Baker et al. |
| 5,629,042 A | 5/1997 | Serpelloni et al. |
| 5,656,284 A | 8/1997 | Balkin |
| 5,711,961 A | 1/1998 | Reiner et al. |
| 5,733,574 A | 3/1998 | Dam |
| 5,811,126 A | 9/1998 | Krishnamurthy |
| 5,840,334 A | 11/1998 | Raiden et al. |
| 5,869,098 A | 2/1999 | Misra et al. |
| 5,939,100 A | 8/1999 | Albrechtsen et al. |
| 6,024,981 A | 2/2000 | Khankari et al. |
| 6,083,531 A | 7/2000 | Humbert-Droz et al. |
| 6,090,401 A | 7/2000 | Gowan, Jr. et al. |
| 6,110,495 A | 8/2000 | Dam |
| 6,131,584 A | 10/2000 | Lauterbach |
| 6,183,775 B1 | 2/2001 | Ventouras |
| 6,221,392 B1 | 4/2001 | Khankari et al. |
| 6,248,760 B1 | 6/2001 | Wilhelmsen |
| 6,264,981 B1 | 7/2001 | Zhang et al. |
| 6,280,761 B1 | 8/2001 | Santus |
| 6,298,859 B1 | 10/2001 | Kierulff et al. |
| 6,426,090 B1 | 7/2002 | Ream et al. |
| 6,569,463 B2 | 5/2003 | Patel et al. |
| 6,583,160 B2 | 6/2003 | Smith et al. |
| 6,585,997 B2 | 7/2003 | Moro et al. |
| 6,586,449 B1 | 7/2003 | Walling |
| 6,676,959 B1 | 1/2004 | Andersson et al. |
| 6,772,767 B2 | 8/2004 | Mua et al. |
| 6,828,336 B2 | 12/2004 | Walling |
| 6,849,286 B1 | 2/2005 | Bayerköhler et al. |
| 6,872,405 B2 | 3/2005 | Takaishi et al. |
| 6,890,559 B1 | 5/2005 | Bayerköhler et al. |
| 6,893,654 B2 | 5/2005 | Pinney et al. |
| 7,025,983 B2 | 4/2006 | Leung et al. |
| 7,122,198 B1 | 10/2006 | Singh et al. |
| 7,163,705 B2 | 1/2007 | Johnson et al. |
| 7,337,782 B2 | 3/2008 | Thompson |
| 7,374,779 B2 | 5/2008 | Chen et al. |
| 7,665,471 B2 | 2/2010 | Mallmann |
| 8,343,532 B2 | 1/2013 | Dam et al. |
| 8,470,366 B2 | 6/2013 | Thakkar |
| 8,501,164 B2 | 8/2013 | Chen |
| 8,545,870 B2 | 10/2013 | Dupinay et al. |
| 2001/0016593 A1 | 8/2001 | Wilhelmsen |
| 2002/0009464 A1 | 1/2002 | Colaco |
| 2003/0176467 A1 | 9/2003 | Andersson et al. |
| 2003/0215553 A1 | 11/2003 | Ribadeau-Dumas et al. |
| 2003/0232082 A1 | 12/2003 | Li et al. |
| 2003/0235617 A1 | 12/2003 | Martino et al. |
| 2004/0052851 A1 | 3/2004 | Graff et al. |
| 2004/0076665 A1 | 4/2004 | Graff et al. |
| 2004/0096501 A1 | 5/2004 | Vaya et al. |
| 2004/0101543 A1* | 5/2004 | Liu ............... A61K 31/465 424/434 |
| 2004/0191322 A1 | 9/2004 | Hansson |
| 2004/0253307 A1 | 12/2004 | Hague et al. |
| 2005/0002993 A1 | 1/2005 | Goggin et al. |
| 2005/0053665 A1 | 3/2005 | Ek et al. |
| 2005/0123502 A1 | 6/2005 | Chan et al. |
| 2006/0120974 A1 | 6/2006 | Mcneight |
| 2006/0171969 A1 | 8/2006 | Macelloni et al. |
| 2006/0171994 A1 | 8/2006 | Dupinay et al. |
| 2006/0191548 A1 | 8/2006 | Strickland et al. |
| 2007/0062549 A1 | 3/2007 | Holton, Jr. et al. |
| 2007/0081949 A1 | 4/2007 | Dam et al. |
| 2007/0178123 A1 | 8/2007 | Levenson et al. |
| 2007/0269386 A1 | 11/2007 | Steen et al. |
| 2007/0269492 A1 | 11/2007 | Steen et al. |
| 2008/0020050 A1 | 1/2008 | Chau et al. |
| 2008/0038209 A1 | 2/2008 | Andersen |
| 2008/0173317 A1 | 7/2008 | Robinson et al. |
| 2008/0286340 A1 | 11/2008 | Andersson et al. |
| 2008/0286341 A1 | 11/2008 | Andersson et al. |
| 2009/0004248 A1 | 1/2009 | Bunick et al. |
| 2009/0014018 A1 | 1/2009 | Sengupta et al. |
| 2009/0023819 A1 | 1/2009 | Axelsson |
| 2009/0025738 A1 | 1/2009 | Mua et al. |
| 2009/0081291 A1 | 3/2009 | Gin et al. |
| 2009/0092573 A1 | 4/2009 | Andersen |
| 2009/0098242 A1 | 4/2009 | Nissen |
| 2009/0263544 A1 | 10/2009 | Soldani |
| 2009/0293889 A1 | 12/2009 | Kumar et al. |
| 2010/0004294 A1 | 1/2010 | Axelsson et al. |
| 2010/0061940 A1 | 3/2010 | Axelsson et al. |
| 2010/0124560 A1 | 5/2010 | Hugerth et al. |
| 2010/0247586 A1* | 9/2010 | Hugerth ............... A23G 1/32 424/401 |
| 2010/0300463 A1* | 12/2010 | Chen ............... A24B 15/306 131/274 |
| 2011/0139164 A1 | 6/2011 | Mua et al. |
| 2011/0220130 A1 | 9/2011 | Mua et al. |
| 2011/0268809 A1 | 11/2011 | Brinkley et al. |
| 2012/0244104 A1 | 9/2012 | Mehta et al. |

FOREIGN PATENT DOCUMENTS

| | | |
|---|---|---|
| WO | WO 91/06288 | 5/1991 |
| WO | WO 02/076211 | 10/2002 |
| WO | WO 2005/023226 | 3/2005 |
| WO | WO 2006/114604 | 11/2006 |
| WO | WO 2007/104574 | 9/2007 |
| WO | WO 2008/112124 | 9/2008 |
| WO | WO 2008/140371 | 11/2008 |
| WO | WO 2008/140372 | 11/2008 |
| WO | WO 2009/037319 | 3/2009 |
| WO | WO 2009/068279 | 6/2009 |
| WO | WO 2010/044736 | 4/2010 |
| WO | WO 2011/139684 | 11/2011 |

* cited by examiner

TRANSLUCENT SMOKELESS TOBACCO PRODUCT

CROSS-REFERENCE TO RELATED APPLICATION

This application is a continuation-in-part of U.S. patent application Ser. No. 13/614,673, filed Sep. 13, 2012, which is a continuation-in-part of U.S. patent application Ser. No. 13/240,525, filed Sep. 22, 2011. Both applications are hereby incorporated by reference in their entireties.

FIELD OF THE INVENTION

The present invention relates to products made or derived from tobacco, or that otherwise incorporate tobacco, and are intended for human consumption. In particular, the invention relates to smokeless tobacco products containing ingredients or components obtained or derived from plants of the *Nicotiana* species.

BACKGROUND OF THE INVENTION

Cigarettes, cigars and pipes are popular smoking articles that employ tobacco in various forms. Such smoking articles are used by heating or burning tobacco, and aerosol (e.g., smoke) is inhaled by the smoker. Tobacco also may be enjoyed in a so-called "smokeless" form. Particularly popular smokeless tobacco products are employed by inserting some form of processed tobacco or tobacco-containing formulation into the mouth of the user. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; 2009/0293889 to Kumar et al.; 2010/0291245 to Gao et al; and 2011/0139164 to Mua et al.; PCT WO 04/095959 to Arnarp et al. and WO 2010/132444 A2 to Atchley, each of which is incorporated herein by reference. Exemplary smokeless tobacco products that have been marketed include those referred to as CAMEL Snus, CAMEL Orbs, CAMEL Strips and CAMEL Sticks by R. J. Reynolds Tobacco Company; GRIZZLY moist tobacco, KODIAK moist tobacco, LEVI GARRETT loose tobacco and TAYLOR'S PRIDE loose tobacco by American Snuff Company, LLC; KAYAK moist snuff and CHATTANOOGA CHEW chewing tobacco by Swisher International, Inc.; REDMAN chewing tobacco by Pinkerton Tobacco Co. LP; COPENHAGEN moist tobacco, COPENHAGEN Pouches, SKOAL Bandits, SKOAL Pouches, RED SEAL long cut and REVEL Mint Tobacco Packs by U.S. Smokeless Tobacco Company; and MARLBORO Snus and Taboka by Philip Morris USA.

It would be desirable to provide an enjoyable form of a tobacco product, such as a smokeless tobacco product, and to provide processes for preparing tobacco-containing compositions suitable for use in smokeless tobacco products.

SUMMARY OF THE INVENTION

The present invention provides a smokeless tobacco product comprising tobacco or a derivative thereof obtained from plants of the *Nicotiana* species. The products of the invention are dissolvable compositions adapted for oral consumption and exhibit a level of translucency despite containing a tobacco or tobacco-derived material. In certain embodiments, the products comprise a tobacco extract that can be characterized as translucent or transparent.

In one aspect, the invention provides a smokeless tobacco product comprising a tobacco material comprising a translucent tobacco extract; a sugar substitute in an amount of at least about 80% by weight of the smokeless tobacco product; and a sugar alcohol syrup, wherein the smokeless tobacco product is orally dissolvable and substantially translucent. The amount and type of the sugar substitute can vary. In certain embodiments, the sugar substitute is a non-hygroscopic sugar alcohol capable of forming a glassy matrix. For example, in some embodiments, the sugar substitute is isomalt. In certain embodiments, the sugar substitute is present in an amount of at least about 85% by weight or at least about 90% by weight. In some embodiments, the sugar alcohol syrup is maltitol syrup.

In one particular embodiment, invention provides a smokeless tobacco product comprising: a tobacco extract in an amount of at least about 3% by weight; a sugar substitute in an amount of at least about 80% by weight; and a sugar alcohol syrup. In another embodiment, the smokeless tobacco product comprises at least about 1.0 percent by weight of the translucent tobacco extract, wherein the translucent tobacco extract consists of components having a molecular weight of no more than about 50,000 Da; a non-hygroscopic sugar alcohol capable of forming a glassy matrix in an amount of at least about 85% by weight; and a sugar alcohol syrup in an amount sufficient to slow recrystallization of the non-hygroscopic sugar alcohol. In yet another embodiment, the smokeless tobacco product comprises at least about 0.5 percent by weight of the translucent tobacco extract, wherein the translucent tobacco extract consists of components having a molecular weight of no more than about 50,000 Da; at least about 1.0 percent by weight of a particulate tobacco material; a non-hygroscopic sugar alcohol capable of forming a glassy matrix in an amount of at least about 85% by weight; and a sugar alcohol syrup in an amount sufficient to slow recrystallization of the non-hygroscopic sugar alcohol. In a still further embodiment, the invention provides a smokeless tobacco product comprising: a tobacco extract consisting of components having a molecular weight of no more than about 50,000 Da in an amount of at least about 3% by weight; a non-hygroscopic sugar alcohol capable of forming a glassy matrix in an amount of at least about 80% by weight; and a sugar alcohol syrup in an amount sufficient to slow recrystallization of the non-hygroscopic sugar alcohol.

In another aspect of the invention is provided a smokeless tobacco product comprising: a first portion comprising at least about 80% by weight isomalt and a sugar alcohol syrup; and a second portion comprising at least about 80% by weight isomalt and a sugar alcohol syrup, wherein the two portions are visually distinguishable by color, and wherein at least one portion comprises a translucent tobacco extract, such as a translucent tobacco extract in the form of an aqueous nicotine solution. The portions can, in some embodiments, comprise different amounts of translucent tobacco extract and/or different amounts of buffer. The portions can, in some embodiments, comprise flavorants in different types and/or amounts. The portions can, in some embodiments, comprise colorants in different types and/or amounts. In certain embodiments, the first portion can comprise no added colorants.

The configuration of such multi-component products can vary. For example, in some embodiments, the second portion is completely encased within the first portion and in some embodiments, both portions are exposed on the surface of the smokeless tobacco product. The ratio of the first portion to second portion can be, for example, between about 1:20 and about 20:1 by volume or between about 1:10 and about 10:1 by volume. In one specific embodiment, the first portion comprises isomalt, maltitol syrup, sodium chloride, vanillin, sucralose, citric acid, tobacco material comprising a translucent tobacco extract, and flavorant; and the second portion comprises isomalt, maltitol syrup, sodium chloride, vanillin, sucralose, citric acid, tobacco material comprising a translucent tobacco extract, flavorant, and a colorant. In certain embodiments, one or both of the portions comprise one or more of the following: a flavorant in an amount from about 0.05 to about 15 percent by weight of the smokeless tobacco product; sucralose in the amount from about 0.01 to about 2 percent by weight of the smokeless tobacco product; and sodium chloride in the amount from about 0.5 to about 10 percent by weight of the smokeless tobacco product.

The form of the smokeless tobacco product can be, for example, a lozenge with a weight of between about 1.8 and about 2.2 g. The lozenge can comprise, for example, between about 0.5 mg and about 5 mg nicotine. In some embodiments, the lozenge comprises isomalt in an amount of at least about 90% by weight or at least about 95% by weight of the smokeless tobacco product.

The smokeless tobacco products described herein can optionally further include a throat irritation mitigant, such as sodium citrate, honey, ginger, pectin, capsaicin, camphor, dextromethorphan, echinacea, zinc gluconate, peppermint oil, spearmint oil, eucalyptus oil, glycerin, organic acids, and combinations or extracts thereof.

The translucent tobacco extract used in the smokeless tobacco products of the present disclosure can be characterized by the molecular weight of its components. For example, the translucent tobacco extract can consist of compounds having a molecular weight of less than about 50,000 Da., or compounds having a molecular weight of less than about 5,000 Da. The translucency of the tobacco extract can be characterized by a percent light transmittance (compared to water at 100% transmittance), such as a percent light transmittance of at least about 30% at visible light wavelengths greater than about 600 nm, or a percent light transmittance of at least about 40% at visible light wavelengths greater than about 600 nm, or a percent light transmittance of at least about 50% at visible light wavelengths greater than about 600 nm (or even higher levels such as greater than about 60% or greater than about 70% or greater than about 80% at visible light wavelengths greater than about 600 nm).

In certain embodiments, the tobacco extract is an ultra-filtered tobacco extract that can be characterized as translucent or transparent. The extract can be, in some embodiments, a heat-treated tobacco extract that has been treated prior to inclusion in the smokeless tobacco product by heating the tobacco extract in an aqueous solution comprising lysine, cysteine, asparaginase, or hydrogen peroxide. The aqueous solution can comprise additional additives; for example, in some embodiments, the aqueous solution further comprises NaOH. In one exemplary embodiment, a smokeless tobacco product is provided, wherein the tobacco extract is a heat-treated tobacco extract that has been treated prior to inclusion in the smokeless tobacco product by heating the tobacco extract in an aqueous solution comprising lysine and NaOH.

In certain embodiments, the tobacco material in the smokeless tobacco product is a combination of a tobacco extract and particulate tobacco. The weight ratio of translucent tobacco extract to particulate tobacco is typically from about 5:1 to about 1:10 (e.g., about 2:1 to about 5:1 or about 1:2 to about 1:6). In multi-component products, one or both portions can optionally comprise a tobacco extract and particulate tobacco. In certain embodiments, the product can include a tobacco extract in an amount of at least about 0.5 weight percent and a particulate tobacco in an amount of at least about 1 weight percent.

The smokeless tobacco product can further comprise any one or more additional components. For example, in some embodiments, the smokeless tobacco product comprises one or more flavorants. The amount of flavorant can vary; for example, flavorant can be included in an amount of from about 0.1 to about 15 percent by weight of the smokeless tobacco product. In certain embodiments, it can be included in an amount up to about 2% or up to about 5% by weight of the smokeless tobacco product. The flavorant can be, in certain embodiments, vanillin and/or mint flavor. In some embodiments, the smokeless tobacco product further comprises at least one sweetener. One exemplary sweetener that can be used according to the invention is sucralose. In one embodiment, the product contains sucralose in the amount from about 0.01 to about 2 percent by weight of the smokeless tobacco product. In some embodiments, the smokeless tobacco product further comprises sodium chloride (NaCl). The NaCl can be present in varying amounts; for example, in some embodiments, the amount of NaCl is from about 0.5 to about 10 percent by weight of the smokeless tobacco product. In certain embodiments, the amount of NaCl can be included in an amount of up to about 4% or up to about 8% by weight of the smokeless tobacco product. The products can further optionally include a coating on at least a portion of the product.

In a further aspect of the invention, the invention provides a method of preparing a translucent smokeless tobacco product, comprising: mixing a translucent tobacco extract, optionally a particulate tobacco, a non-hygroscopic sugar alcohol capable of forming a glassy matrix in a melted state, and a sugar alcohol syrup to form a mixture; and cooling the mixture to room temperature to form a solid smokeless tobacco product exhibiting translucency.

In another aspect is provided a method of preparing a translucent smokeless tobacco product, comprising: mixing isomalt, and a sugar alcohol syrup to form a first mixture comprising at least about 80% isomalt by weight; separately mixing isomalt and a sugar alcohol syrup to form a second mixture comprising at least about 80% isomalt by weight; incorporating a translucent tobacco extract into one or both of the first and second mixtures; combining and cooling the mixtures to room temperature to form a solid smokeless tobacco product with two portions, wherein the two portions are visually distinguishable by color. The translucent tobacco extract can, in some embodiments, be incorporated into both the first and second mixtures. A colorant can be incorporated into at least one of the first and second mixtures, e.g., a colorant can be incorporated into both of the first and second mixtures in different amounts.

The translucent tobacco extract can, in some embodiments, be treated prior to use in the methods disclosed herein. For example, the tobacco extract can be treated by size exclusion chromatography, microfiltration, ultrafiltration, nanofiltration, reverse osmosis, or a combination thereof to produce the translucent tobacco extract. In certain embodiments, the treatment removes components having a molecular weight above about 50,000 Da. In some embodiments, the treatment is conducted in combination with one or more additional treatments. For example, in some embodiments, the translucent tobacco extract is subjected to treatment with a non-imprinted polymer adapted for the removal of tobacco-specific nitrosamines prior to use in the method.

In some embodiments, the translucent or transparent tobacco extract has been heat treated prior to use in the method. For example, the tobacco extract can be heated in an aqueous solution comprising lysine, cysteine, asparaginase, or hydrogen peroxide. In some embodiments, the tobacco extract is heated in such an aqueous solution, which can further comprise NaOH. In certain embodiments, the heat treating step is conducted at about 88° C. Using a heat treated tobacco extract can, in some embodiments, give a smokeless tobacco product having less than about 500 ppb acrylamide.

In some embodiments, the method of preparing a translucent smokeless tobacco product comprises heating the non-hygroscopic sugar alcohol to a temperature above the hard crack stage in the absence of the translucent tobacco extract and mixing the tobacco extract into the non-hygroscopic sugar alcohol at a temperature below the hard crack stage. The temperatures can vary; however, in certain embodiments, the hard crack stage is about 145° C. to about 155° C. and the non-hygroscopic sugar alcohol is heated at a temperature between the hard crack stage and about 171° C. In some embodiments, the method further comprises introducing the mixture into a plurality of molds to create individual product units prior to the cooling step.

In another aspect of the invention, the invention provides a method of preparing a translucent or transparent extract for incorporating into a smokeless tobacco product, comprising: extracting a tobacco material with an aqueous solvent to form an aqueous tobacco extract; ultrafiltering the aqueous tobacco extract to remove components having a molecular weight above about 50,000 Da to form a translucent or transparent tobacco extract; and heat treating the tobacco extract prior to or after the ultrafiltering step by heating the extract in an aqueous solution comprising L-lysine, L-cysteine, asparaginase, or hydrogen peroxide. In certain embodiments, the ultrafiltering step comprises passing the aqueous tobacco extract through multiple ultrafiltration membranes.

BRIEF DESCRIPTION OF THE DRAWINGS

In order to provide an understanding of embodiments of the invention, reference is made to the appended drawings, which are exemplary only and should not be construed as limiting the invention.

DETAILED DESCRIPTION OF THE PREFERRED EMBODIMENTS

Figure 1:
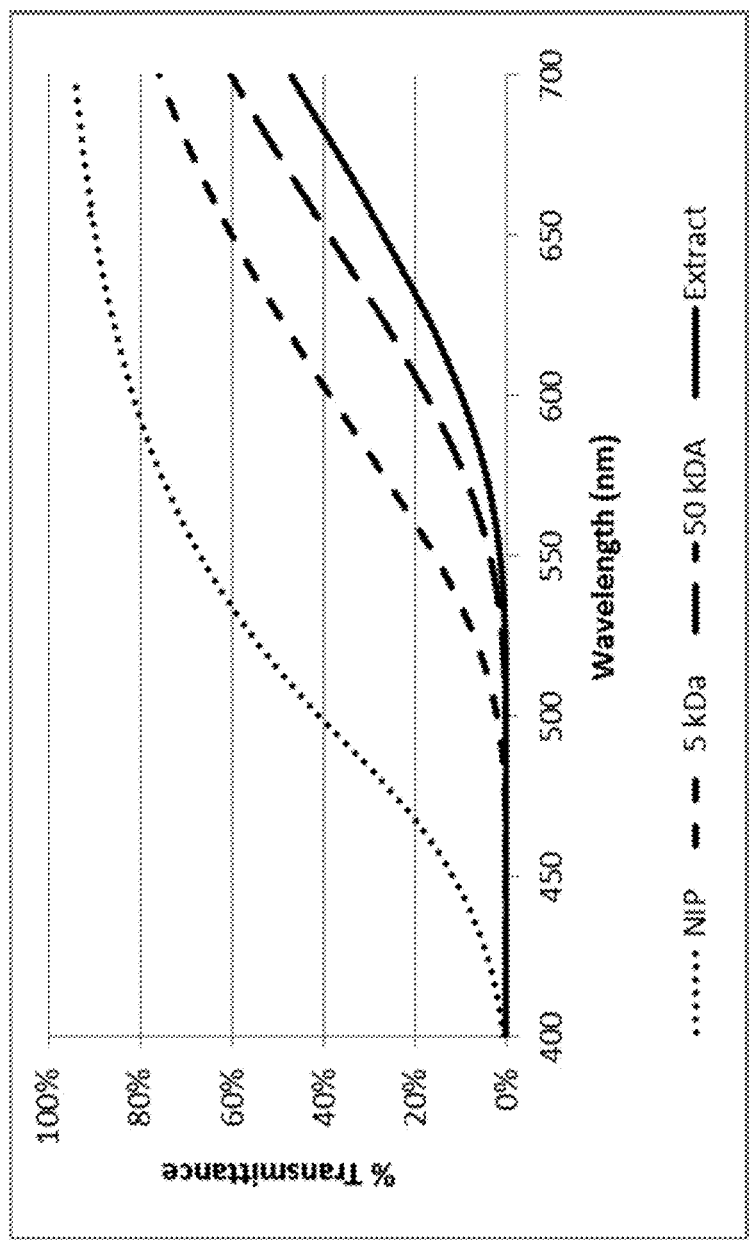
FIG. 1 graphically illustrates visible light transmission spectra of a tobacco extract at various stages of processing according to the invention.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention relates to smokeless tobacco products adapted for oral consumption that contain tobacco or a tobacco-derived material and that exhibit translucence or transparency, such as a product in the form of a translucent lozenge. The invention provides a process for preparing a tobacco material that can impart tobacco flavor to the product without reducing clarity of the product to the point of opacity, and a process for preparing a translucent product using such a tobacco material.

The selection of the plant from the *Nicotiana* species utilized in the products and processes of the invention can vary; and in particular, the types of tobacco or tobaccos may vary. The type of tobacco used as both the source of tobacco stalks and as the carrier for the syrup of the invention can vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Various representative types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al.; U.S. Pat. No. 7,025,066 to Lawson et al.; and U.S. Pat. No. 7,798,153 to Lawrence, Jr.; and US Patent Appl. Pub. No. 2008/0245377 to Marshall et al.; each of which is incorporated herein by reference.

Exemplary *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp.

*Hersperis, N. pauciflora, N. petunioides, N. quadrivalvis, N. repanda, N. rotundifolia, N. solanifolia* and *N. spegazzinii*.

*Nicotiana* species can be derived using genetic modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and 2008/0209586 to Nielsen et al., which are all incorporated herein by reference.

For the preparation of smokeless tobacco products, it is typical for harvested plants of the *Nicotiana* species to be subjected to a curing process. Descriptions of various types of curing processes for various types of tobaccos are set forth in *Tobacco Production, Chemistry and Technology*, Davis et al. (Eds.) (1999). Exemplary techniques and conditions for curing flue-cured tobacco are set forth in Nestor et al., *Beitrage Tabakforsch. Int*, 20, 467-475 (2003) and U.S. Pat. No. 6,895,974 to Peele, which are incorporated herein by reference. Representative techniques and conditions for air curing tobacco are set forth in Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing. Typically, harvested tobaccos that are cured are then aged.

At least a portion of the plant of the *Nicotiana* species (e.g., at least a portion of the tobacco portion) can be employed in an immature form. That is, the plant, or at least one portion of that plant, can be harvested before reaching a stage normally regarded as ripe or mature. As such, for example, tobacco can be harvested when the tobacco plant is at the point of a sprout, is commencing leaf formation, is commencing flowering, or the like. At least a portion of the plant of the *Nicotiana* species (e.g., at least a portion of the tobacco portion) can be employed in a mature form. That is, the plant, or at least one portion of that plant, can be harvested when that plant (or plant portion) reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position.

The *Nicotiana* species can be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be employed. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment.

The post-harvest processing of the plant or portion thereof can vary. After harvest, the plant, or portion thereof, can be used in a green form (e.g., the plant or portion thereof can be used without being subjected to any curing process). For example, the plant or portion thereof can be used without being subjected to significant storage, handling or processing conditions. In certain situations, it is advantageous for the plant or portion thereof be used virtually immediately after harvest. Alternatively, for example, a plant or portion thereof in green form can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use.

The harvested plant or portion thereof can be physically processed. The plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

The plant of the *Nicotiana* species or portions thereof can be subjected to other types of processing conditions. For example, components can be separated from one another, or otherwise fractionated into chemical classes or mixtures of individual compounds. Typical separation processes can include one or more process steps such as solvent extraction using polar solvents, organic solvents, or supercritical fluids, chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No.

5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated herein by reference. See also, the types of separation techniques set forth in Brandt et al., *LC-GC Europe*, p. 2-5 (March, 2002) and Wellings, *A Practical Handbook of Preparative HPLC* (2006), which are incorporated herein by reference. In addition, the plant or portions thereof can be subjected to the types of treatments set forth in Ishikawa et al., *Chem. Pharm. Bull.*, 50, 501-507 (2002); Tienpont et al., *Anal. Bioanal. Chem.*, 373, 46-55 (2002); Ochiai, *Gerstel Solutions Worldwide*, 6, 17-19 (2006); Coleman, III, et al., *J. Sci. Food and Agric.*, 84, 1223-1228 (2004); Coleman, III et al., *J. Sci. Food and Agric.*, 85, 2645-2654 (2005); Pawliszyn, ed., *Applications of Solid Phase Microextraction, RSC Chromatography Monographs*, (Royal Society of Chemistry, UK) (1999); Sahraoui et al., *J. Chrom.*, 1210, 229-233 (2008); and U.S. Pat. No. 5,301,694 to Raymond et al., which are all incorporated herein by reference.

According to the present invention, the *Nicotiana* plant or portion thereof is typically subjected to processing intended to provide improved clarity of the tobacco material. In certain embodiments, the tobacco material used in the products of the invention is in the form of an extract, such as an aqueous extract of a tobacco material. Improved clarity of a tobacco extract can be obtained, for example, by removing high molecular weight components from the tobacco extract. In certain embodiments, high molecular weight components that are beneficially removed according to the present invention include, but are not limited to, high molecular weight Maillard browning polymers, proteins, polysaccharides, certain pigments, and bacteria. Various methods can be used for this purpose, including size exclusion chromatography, microfiltration, ultrafiltration, nanofiltration, reverse osmosis, and combinations thereof.

In one embodiment, ultrafiltration is used to remove high molecular weight components in the tobacco material. The ultrafiltration method is typically applied to a tobacco material comprising a tobacco extract (e.g., an aqueous tobacco extract). In ultrafiltration, the material to be filtered is brought into contact with a semipermeable membrane. The membrane can be of any type, such as plate-and-frame (having a stack of membranes and support plates), spiral-wound (having consecutive layers of membrane and support material rolled up around a tube), tubular (having a membrane-defined core through which the feed flows and an outer, tubular housing where permeate is collected), or hollow fiber (having several small diameter tubes or fibers wherein the permeate is collected in the cartridge area surrounding the fibers). The membrane can be constructed of various materials. For example, polysulfone, polyethersulfone, polypropylene, polyvinylidenefluoride, and cellulose acetate membranes are commonly used, although other materials can be used without departing from the invention described herein.

Ultrafiltration membranes are available in a wide range of pore sizes (typically ranging from about 0.1 to about 0.001 microns). Membranes are more typically described by their molecular weight cutoffs. Ultrafiltration membranes are commonly classified as membranes with number average molecular weight cutoffs of from about $10^3$ Da to about $10^5$ Da. In practice, compounds with molecular weights above the molecular weight cutoff are retained in the retentate, and the compounds with molecular weights below the cutoff pass through the filter into the permeate. Ultrafiltration methods typically are not capable of removing low molecular weight organic compounds and ions.

Ultrafiltration is typically a cross-flow separation process. The liquid stream to be treated (feed) flows tangentially along the membrane surface, separating into one stream that passes through the membrane (permeate) and another that does not (retentate or concentrate). The operating parameters of the ultrafiltration system can be varied to achieve the desired result. For example, the feed mixture to be filtered can be brought into contact with the membrane by way of applied pressure. The rate of permeation across the membrane is directly proportional to the applied pressure; however, the maximum pressure may be limited. The flow velocity of the mixture across the membrane surface can be adjusted. Temperature can also be varied. Typically, permeation rates increase with increasing temperature.

Commercial ultrafiltration systems are readily available and may be used for the ultrafiltration methods of the present invention. For example, commercial suppliers such as Millipore, Spectrum® Labs, Pall Corporation, Whatman®, Porex Corporation, and Snyder Filtration manufacture various filter membranes and cartridges, and/or filtration systems (e.g., tangential flow filtration systems). Exemplary membranes include, but are not limited to, Biomax® and Ultracel® membranes and Pellicon® XL cassettes (from Millipore), Microkros®, Minikros®, and KrosFlo® Hollow Fiber Modules (from Spectrum® Labs), and Microza filters and Centramate,™ Centrasette,™ Maximate™, and Maxisette™ Tangential Flow Filtration Membrane Cassettes. Commercially available filtration systems include, but are not limited to, Millipore's Labscale™ Tangential Flow Filtration (TFF) system and Spectrum® Labs' KrosFlo® and MiniKros® Tangential Flow Filtration Systems.

Filters and/or membranes that may be useful according to the present invention include those with molecular weight cutoffs of less than about 100,000 Da, less than about 75,000 Da, less than about 50,000, less than about 25,000 Da, less than about 20,000 Da, less than about 15,000 Da, less than about 10,000 Da, and less than about 5,000 Da. In certain embodiments, a multistage filtration process is used to provide an extract with improved clarity. Such embodiments employ multiple filters and/or membranes of different (typically decreasing) molecular weight cutoffs. Any number of filters and/or membranes can be used in succession according to the invention. For example, a first filtration may be conducted using a 50,000 Da molecular weight cutoff filter and a second filtration may be conducted using a 5,000 Da molecular weight cutoff filter.

According to the present invention, the ultrafiltration process is designed to achieve a tobacco extract having a decreased level of suspended solids, and thus an increased level of clarity. For example, depending on the molecular weight cutoff of the filters, the ultrafiltered extract may comprise only compounds with molecular weights below about 50,000, below about 25,000, below about 10,000 Da, below about 7,500 Da, below about 5,000 Da, below about 2,500 Da, or below about 1,000 Da. The ultrafiltered extract typically comprises primarily sugars, nicotine, and amino acids.

The ultrafiltered extract exhibits a level of improvement in clarity over the non-ultrafiltered extract. Clarity of the extract, and tobacco products according to the invention made therefrom, is typically defined in terms of translucency. As used herein, "translucent" or "translucency" refers to materials allowing some level of light to travel therethrough diffusely. In certain embodiments, certain materials of the invention (e.g., certain tobacco extracts or final smokeless tobacco products made therefrom) can have such a high degree of clarity that the material can be classified as "transparent" or exhibiting "transparency," which is defined as a material allowing light to pass freely through without significant diffusion. The clarity of the ultrafiltered extract is such that there is some level of translucency as opposed to opacity (which refers to materials that are impenetrable by light).

The improvement in clarity of the ultrafiltered extract over the non-ultrafiltered extract can be quantified by any known method. For example, optical methods such as turbidimetry (or nephelometry) and colorimetry may be used to quantify the cloudiness (light scattering) and the color (light absorption), respectively, of the ultrafiltered extract or products made therefrom. Translucency can also be confirmed by visual inspection by simply holding the material (e.g., extract) or product up to a light source and determining if light travels through the material or product in a diffuse manner.

In certain embodiments, the ultrafiltered extract is analyzed by contacting the extract with light and measuring the percent of light that has not been absorbed and/or dispersed by the extract. The measurement can be done, for example, using a standard spectrophotometer at a given wavelength. The spectrophotometer is typically calibrated with deionized water, which is assigned a transparency value of 100%. Acceptable levels of translucency/transparency at a given wavelength in the ultrafiltered extract can vary. Typically, the extract of the invention has a translucency (measured as percent light transmittance) of greater than about 5%, greater than about 10%, greater than about 15%, greater than about 20%, greater than about 25%, greater than about 30%, greater than about 40%, greater than about 50%, greater than about 60%, greater than about 60%, greater than about 70%, greater than about 80%, or greater than about 90%. One or more of these transparency levels is typically achieved in certain embodiments, for example, at visible light wavelengths above about 400 nm (e.g., at a wavelength of about 500 nm to about 700 nm such as about 500 nm, about 550 nm, about 600 nm, about 650 nm, and about 700 nm). Typically, the ultrafiltered extract will not be colorless, and will have some discernible brown/black coloring. Following ultrafiltration, the extract can be stored in the refrigerator or freezer or the extract can be freeze dried or spray dried prior to use in the products of the invention. In certain embodiments, it is provided in syrup form.

Although in some embodiments, the tobacco extract is used directly, it may be desirable to heat treat the extract. This thermal treatment can be conducted before the ultrafiltration, after the ultrafiltration, or both before and after the ultrafiltration. For example, a tobacco material can be thermally processed by mixing the tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents (e.g., hydrogen peroxide), oxidation catalysts, plant extracts, and combinations thereof, to form a moist tobacco mixture; and heating the moist tobacco mixture at a temperature of at least about 60° C. to form a heat-treated tobacco mixture. In one embodiment, the treated tobacco extract is heat treated in the presence of water, NaOH, and an additive (e.g., lysine) at about 88° C. for about 60 minutes. Such heat treatment can help prevent acrylamide production resulting from reaction of asparagine with reducing sugars in tobacco materials and can provide some degree of pasteurization. See, for example, US Pat. Pub. No. 2010/0300463 to Chen et al., which is incorporated herein by reference. In certain embodiments wherein a heat-treated tobacco extract is used in a smokeless tobacco product of the present invention, the product can be characterized by very low acrylamide content. For example, in some embodiments, the smokeless tobacco product is characterized by an acrylamide content of less than about 500 ppb (ng/g), less than about 400 ppb, less than about 300 ppb, less than about 200 ppb, or less than about 100 ppb.

In addition to asparaginase noted above, the tobacco extract could also be treated with other enzymes and/or probiotics to inhibit acrylamide formation or otherwise chemically alter the tobacco extract as discussed in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference. As used herein, the term "probiotic" or "probiotic microorganism" is intended to encompass all live microorganisms that may be classified as probiotics by various sources. For example, the Food and Agriculture Organization of the United Nations (FAO) defines probiotics as "live microorganisms, which, when administered in adequate amounts, confer a health benefit on the host." In some reports, such health benefits can include, but are not limited to: colonization of the intestinal, respiratory, and/or urogenital tracts, cholesterol metabolism, lactose metabolism, absorption of calcium, synthesis of vitamins, reduction of yeast and vaginal infections, reduction of digestive problems (e.g., constipation and diarrheal diseases), production of natural antibiotics, lactic acid, enzymes, hydrogen peroxide, inhibition of pathogenic microorganisms by production of antibiotic-like substances; and a decrease in pH. Although the traditional definition of "probiotic" relates to human and animal digestive organisms, this term has been applied in other contexts, such as in the field of agriculture. Certain types of probiotics and compositional ingredients that can be added include examples set forth in U.S. Pat. No. 8,097,245 to Harel et al.; U.S. Pat. No. 8,097,281 to Heim et al.; U.S. Pat. No. 8,101,167 to Gueniche; and U.S. Pat. No. 8,101,170 to Plail et al., which are all incorporated herein by reference.

It is preferred that probiotics used according to the invention are "GRAS" (Generally Regarded as Safe), although non-GRAS probiotics can be used in certain embodiments. Probiotics are typically identified by their genus, species, and strain level. Certain recognized probiotic genera include *bifidobacterium, lactobacillus, enterococcus, proionobacterium, bacillus, saccharomyces*, and *streptococcus*. Many common probiotics are selected from *lactobacillus* species, *bifidobacterium* species, and *streptococcus thermophilus*.

Exemplary enzymes that can be used to treat the tobacco extract include amylases (which catalyze the breakdown of starch into sugars) or proteases (which catalyze the hydrolysis of peptide bonds of proteins) or a combination thereof.

Amylases can include α-amylase, β-amylase, γ-amylase, or a combination thereof. Proteases can include serine proteases, threonine proteases, cysteine proteases, asparatate proteases, metalloproteases, and glutamic acid proteases and certain exemplary proteases include, but are not limited to, protease *bacillus licheniformis*, protease *bacillus* sp., protease *Aspergillus oryzae*, protease *bacillus amyloliquefaciens*, protease *bacillus*, and protease *Streptomyces griseus*, which can include commercially available enzyme products Alcalase™, Esperase™, Everlase™, Flavourzyme™, Neutrase™, Protamex™, Savinase™, and Substilisin A™ from Novozymes A/S. In certain embodiments, the enzyme is a polyphenol oxidase (PPO), an oxidase such as a monophenol oxidase enzyme (tyrosinase), or an o-diphenol oxygen oxidoreductase enzyme (catechol oxidase). Another exemplary oxidase for use according to the invention is laccase.

The tobacco extract can also be subjected to further treatment steps, such as treatment steps adapted to remove specific classes of compounds from the tobacco extract. For example, in some embodiments, the tobacco extract is brought into contact with an imprinted polymer or non-imprinted polymer such as described, for example, in US Pat. Pub. Nos. 2007/0186940 to Bhattacharyya et al; 2011/0041859 to Rees et al.; and 2011/0159160 to Jonsson et al; and U.S. patent application Ser. No. 13/111,330 to Byrd et al., filed May 19, 2011, all of which are incorporated herein by reference. Treatment with a molecularly imprinted polymer (MIP) or non-imprinted polymer (NIP) can be used to remove certain components of the extract, such as tobacco-specific nitrosamines (TSNAs), including N'-nitrosonornicotine (NNN), (4-methylnitrosamino)-1-(3-pyridyl)-1-butanone (NNK), N'-nitrosoanatabine (NAT), and N'-nitrosoanabasine (NAB); polyaromatic hydrocarbons (PAHs), including benz[a]anthracene, benzo[a]pyrene, benzo[b]fluoranthene, benzo[k]fluoranthene, chrysene, dibenz[a,h]anthracene, and indeno[1,2,3-cd]pyrene; or other Hoffmann analytes. Still further, the tobacco extract could be treated with ion exchange materials having amine functionality, which can remove certain aldehydes and other compounds. See, for example, U.S. Pat. No. 4,033,361 to Horsewell et al and U.S. Pat. No. 6,779,529 to Figlar et al., which are incorporated by reference herein.

Accordingly, "treated tobacco extract" as used herein refers to a tobacco extract that has been treated in some way to remove high molecular weight components and thereby improve clarity (e.g., an ultrafiltered extract). The treated tobacco extract may or may not be heat-treated (or treated with a MIP, NIP, or other material adapted to remove certain components of the extract) as described herein. In certain embodiments, the treated tobacco extract comprises nicotine in a high concentration. For example, in some embodiments, the tobacco extract comprises highly purified nicotine, e.g., at least about 90% nicotine by dry weight, at least about 95% nicotine by dry weight, at least about 98% nicotine by dry weight, at least about 99% nicotine by dry weight, or at least about 99.9% nicotine by dry weight. Accordingly, in some embodiments, the tobacco extract comprising highly purified nicotine is referred to as a tobacco-derived nicotine-containing solution. It is understood that such extracts comprising a high concentration of nicotine can have varying concentrations of nicotine, depending on the water content thereof.

The treated tobacco extract is used in the production of smokeless tobacco products. Accordingly, the present invention provides translucent or transparent smokeless tobacco products comprising tobacco-derived material.

Exemplary smokeless tobacco products of the invention have the form of a lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; which are incorporated herein by reference. The amount of material contained within each piece (e.g., each unit of lozenge type of product) can vary. For example, a representative unit for lozenge products generally weighs at least about 100 mg, often at least about 200 mg, and frequently at least about 300 mg; while the weight of a representative unit for such products generally does not exceed about 1.5 g, often does not exceed about 1 g, and frequently does not exceed about 0.75 g.

The amount of treated tobacco extract within the overall composition can vary. The treated tobacco extract can be provided in varying concentrations, which can affect the amount of extract included in the mixture. The amount of extract is at least about 0.5%, generally at least about 1%, often at least about 1.5%, often at least about 2%, often at least about 2.5%, and frequently at least about 3% by weight of the product mixture. In certain embodiments, the amount of extract is at least about 4%, at least about 5%, at least about 6%, or at least about 7% by weight of the product mixture. The amount of treated tobacco extract added to the product mixture is typically not more than about 20%. Exemplary types of such products can incorporate about 3% by weight, about 4% by weight, about 4.5% by weight of the mixture, or about 7.5% by weight of the mixture.

Although the treated tobacco extract can be used as the sole tobacco source in products of the invention, in certain embodiments, the treated tobacco extract can be combined with one or more additional tobacco materials (e.g., solid tobacco material, such as filler-type pieces, granules, or fine powders). For example, in some embodiments, a smokeless tobacco product is provided that comprises treated tobacco extract and milled tobacco. The manner by which the tobacco material is provided in a particulate form may vary. Typically, plant parts or pieces are comminuted, ground or pulverized into a particulate form using equipment and techniques for grinding or milling such as hammer mills, cutter heads, air control mills, or the like. The plant material is relatively dry in form during grinding or milling. For example, tobacco parts or pieces can be ground or milled when the moisture content thereof is less than about 15 weight percent to less than about 5 weight percent. The milled tobacco material is typically employed in the form of parts or pieces that have an average particle size less than about 50 microns. In one embodiment, the average particle size of the tobacco particles may be less than or equal to about 25 microns. In less preferred embodiments, the smokeless tobacco products contain a solid particulate material as the sole tobacco material in the product (i.e., in the absence of translucent tobacco extract).

The additional tobacco materials can be included in various amounts; for example, in certain embodiments, the additional tobacco materials are included in an amount of between about 0.25% and about 10% by weight (e.g., between about 0.5% and about 6% by weight) based on the overall weight of the smokeless tobacco product. Where the smokeless tobacco product comprises multiple sources of tobacco (i.e., treated tobacco extract and one or more additional tobacco materials), the ratio of treated tobacco extract to additional tobacco material can vary. In certain embodiments, the weight ratio of treated tobacco extract to solid tobacco (e.g., milled tobacco) is from about 5:1 to about 1:10 (e.g., about 2:1 to about 5:1 or about 1:2 to about 1:6). In certain embodiments, the additional tobacco material is present in an amount of at least about 1 weight percent or at least about 2 weight percent or at least about 3 weight percent or more. In one particular embodiment, the product contains about 0.5 to about 5% by weight of treated tobacco extract (e.g., about 0.5 to about 1.5% by weight or about 1% by weight) and about 1 to about 10% by weight (e.g., about 3 to about 7% by weight or about 5% by weight) milled tobacco.

In such embodiments, it is to be understood that only a portion of the smokeless tobacco product may be completely transparent or translucent since the presence of a solid tobacco particulate will create discrete areas within the product that are not translucent or transparent. Nonetheless, the inclusion level of such solid tobacco components is typically at a level low enough that the product can be viewed as substantially translucent, meaning the product as a whole is translucent except for those portions of the product where the solid, opaque material is located. In embodiments comprising additional tobacco in solid form, the smokeless tobacco product may exhibit a transparent or translucent base with opaque portions therein (indicative of the presence of the solid tobacco material). For example, where the additional tobacco is provided in powdered, pulverized, granulated, ground, or milled form (i.e., a particulate form), it may be evidenced by dark specks or spots within a transparent or translucent product. The opaque portions can be isolated to one or more regions of the product or can be distributed throughout the product (e.g., uniformly distributed). The smokeless tobacco products can, in certain embodiments, be described as substantially translucent or, stated differently, as comprising at least about 50% by volume transparent or translucent material, at least about 60% transparent or translucent material, at least about 70% transparent or translucent material, at least about 80% transparent or translucent material, at least about 90% transparent or translucent material, or at least about 95% transparent or translucent material.

Although sucrose can be used in the preparation of the smokeless tobacco products of the present invention, the smokeless tobacco products are typically sugar-free products, comprising one or more sugar substitutes. "Sugar-free" as used herein is intended to include products having less than about 1/15th sugar by weight, or less than about 1/10th sugar by weight.

Accordingly, in one embodiment, the smokeless tobacco product comprises a sugar substitute. The sugar substitute is typically provided in pure, solid form (e.g., granular or powdered form). In certain embodiments, the sugar substitute is dry, comprising a very low water content. For example, the sugar substitute can comprise less than about 5% water by weight, less than about 3% water by weight, less than about 2% water by weight, or less than about 1% water by weight.

The sugar substitute can be any sugarless material (i.e., sucrose-free material) and can be natural or synthetically produced. The sugar substitute used in the invention can be nutritive or non-nutritive. For example, the sugar substitute is commonly a sugar alcohol. Sugar alcohols that may be useful according to the present invention include, but are not limited to, erythritol, threitol, arabitol, xylitol, ribotol, mannitol, sorbitol, dulcitol, iditol, isomalt, maltitol, lactitol, polyglycitol, and mixtures thereof. For example, in certain embodiments, the sugar alcohol is selected from the group consisting of erythritol, sorbitol, and isomalt. The amount of sugar substitute in the smokeless tobacco product mixture can vary, but is typically at least about 75%, at least about 80%, at least about 85%, or at least about 90% by weight of the mixture.

In certain embodiments, the sugar substitute is capable of forming a glassy matrix. The formation of a glassy matrix is commonly characterized by a translucent/transparent appearance. Typically, the sugar substitute is substantially non-hygroscopic. Non-hygroscopic materials typically do not absorb, adsorb, and/or retain a significant quantity of moisture from the air. For example, in some embodiments, the sugar substitute exhibits a weight gain of water of less than about 50% upon exposure to conditions of 25° C., 80% relative humidity for two weeks. Typically, the sugar substitute exhibits a weight gain of less than about 30%, less than about 20%, less than about 10%, less than about 5%, less than about 2%, or less than about 1% upon exposure to conditions of 25° C., 80% relative humidity for two weeks. Non-hygroscopic materials can provide the benefit of reducing the tendency of the smokeless tobacco product to tackify upon exposure to humidity.

In certain embodiments, the sugar substitute comprises one or more sugar alcohols. For example, in one embodiment, the sugar substitute is isomalt. Isomalt is a disaccharide that is typically made by enzymatic rearrangement of sucrose into isomaltulose, followed by hydrogenation to give an equimolar composition of 6-O-α-D-glucopyranosido-D-sorbitol (1,6-GPS) and 1-O-α-D-glucopyranosido-D-mannitol-dihydrate (1,1-GPM-dihydrate).

In addition to the treated extract and sugar substitute, the smokeless tobacco product of the present invention contains a syrup, e.g., a sugar syrup or a sugar alcohol syrup. "Sugar alcohol syrup" as used herein is intended to refer to a thick solution of sugar alcohol in water, e.g., having greater than about 40% solids, preferably having greater than about 50% solids, greater than about 60% solids, greater than about 70% solids, or greater than about 80% solids. Typically, the solid content of the sugar alcohol syrup primarily comprises the named sugar alcohol (i.e., maltitol syrup typically comprises greater than about 80%, greater than about 85%, or greater than about 90% by weight maltitol on a dry basis). Sugar alcohol syrups are generally prepared by heating a solution of the sugar alcohol in water and cooling the mixture to give a viscous composition. The resulting syrup is typically characterized by a relatively high concentration of sugar alcohol and relatively high stability (i.e., the sugar alcohol typically does not crystallize from solution, e.g., at room temperature).

The syrup, e.g., sugar alcohol syrup, desirably is capable of affecting the recrystallization of a melted sugar substitute. One exemplary sugar alcohol syrup that is particularly useful according to the present invention is maltitol syrup. Other sugar alcohol syrups can be used, including, but not limited to, corn syrup, golden syrup, molasses, xylitol, mannitol, glycerol, erythritol, threitol, arabitol, ribotol, mannitol, sorbitol, dulcitol, iditol, isomalt, lactitol, and polyglycitol syrups. Such sugar alcohol syrups can be prepared or can be obtained from commercial sources. For example, maltitol syrups are commercially available from such suppliers as Corn Products Specialty Ingredients. Although sugar alcohol syrups may be preferred, sugar syrups can, in certain embodiments, be used in place of or in combination with the sugar alcohol syrup. For example, in some embodiments, corn syrup, golden syrup, and/or molasses can be used.

The amount of sugar alcohol syrup added to the smokeless tobacco product mixture is typically that amount required to slow recrystallization of the sugar substitute in melted form. One of skill in the art would understand the need to vary the amount of sugar alcohol syrup depending on the composition of the remaining ingredients to ensure that the recrystallization is sufficiently slow to provide a material with the desired characteristics (e.g., a desired level of translucency/transparency). Accordingly, the amount of sugar alcohol syrup can vary, but typically ranges from about 0.1% to about 2%, often from about 0.5% to about 1.5%, and more often about 1% by weight of the smokeless tobacco product mixture. In certain embodiments, the amount of sugar alcohol syrup is higher, for example, up to about 2% by weight of the mixture, up to about 5% by weight of the mixture, up to about 10% by weight of the mixture, or up to about 20% by weight of the mixture In certain embodiments, the smokeless tobacco product further comprises a salt. The presence of a salt in the smokeless tobacco product may act to suppress bitterness and/or enhance sweetness. Any type of salt can be used. Common table salt (NaCl) is typically used according to the present invention, but other types of salts are intended to be encompassed as well. The amount of salt added may vary, but typically ranges from 0% to about 8%, for example from about 0.5% to about 4% or from about 0.6% to about 2%, often around 1% by weight of the smokeless tobacco product. In some embodiments, a somewhat salty taste is a desirable feature of the smokeless tobacco product.

In some embodiments, the composition according to the invention also contains one or more buffering agents and/or pH adjusters (i.e., acids or bases). In some embodiments, one or more buffering agents and/or pH adjusters are added to the mixture to ensure that the final smokeless tobacco product has a pH within a desirable range. Exemplary pH ranges in such smokeless tobacco products are generally from about 6-11, and often about 7-10 (e.g., about 7 or about 8). In such embodiments, the amount of buffering agent and/or pH adjuster added to the smokeless tobacco product mixture is simply that amount required to bring the formulation to or keep the formulation at the desired pH. The amount of buffering agent and/or pH adjuster added to any given formulation can be readily calculated by one skilled in the art and may comprise, for example, about 0.5% to about 1% by weight of the mixture. It is noted that in certain embodiments, a basic pH is not necessary in the products of the present invention. Accordingly, certain products of the present invention have a pH of less than about 6 or less than about 5 (e.g., from about 4 to about 6).

Various food-grade buffering agents are known and can be used to adjust the pH of the products of the present invention. Suitable buffering agents include those selected from the group consisting of acetates, glycinates, phosphates, glycerophosphates, citrates such as citrates of alkaline metals, carbonates, hydrogen carbonates, and borates, and mixtures thereof. In certain embodiments, the buffering agent is an amino acid, as taught for example, in US Pat. Pub. No. 2008/0286341 to Andersson et al. and PCT Appl. No. WO2008/040371 to Andersson et al., which are both incorporated herein by reference. As noted therein, various amino acids and salts thereof are useful for this purpose, including, but not limited to, arginine, asparagine, glutamic acid, glutamine, glycine, histidine, isoleucine, leucine, lysine, methionine, phenylalanine, serine, threonine, valine, cysteic acid, N-glycylglycine, and ornithine. In certain embodiments, N-glycylglycine or L-lysine is added as a buffering agent. In some embodiments, an amino acid buffering agent is used in combination with another amino acid buffering agent and/or in combination with one or more non-amino acid buffering agents. In certain embodiments, the optional pH adjusting agent is a base (e.g., NaOH). In certain embodiments, L-lysine and NaOH are added to the compositions of the present invention.

Certain tobacco extracts, particularly those subjected to heat treatment, can be buffered using various buffering systems. For example, one representative buffering system is sodium tripolyphosphate, but it is understood that other suitable types of buffering agents (including other phosphates) can be used. In certain embodiments, the buffer can be added in the form of an aqueous solution. For example, in one representative example, an aqueous buffer solution is added to a mixture of isomalt and maltitol syrup upon melting (e.g., at greater than about 175° C.). The resulting mixture is cooled (e.g., to less than about 140° C.) and other components, including the treated tobacco extract (or a combination of a treated tobacco extract and milled tobacco) are added to the mixture. The mixture is further cooled and molded as described in more detail previously. The pH of an exemplary sample prepared in this manner, when tested for pH by placing a 5 g of that sample in 100 g of water, exhibits a pH of about 7.8. The amount of buffering agent added can vary, but is generally an amount sufficient to maintain the pH within one of the exemplary pH ranges noted above. For example, an aqueous buffer system can be provided by dissolving about 22 weight parts sodium tripolyphosphate in about 73 weight parts water; and the buffer system can be added to a melted mixture of about 275 weight parts isomalt and about 3 weight parts of maltitol syrup. The buffered isomalt mixture is heated to about 177° C. and then cooled to about 138° C.; and then a mixture of about 6 weight parts tobacco extract (or a combination of tobacco extract and milled tobacco), about 12 weight parts water, about 0.12 weight parts sucralose and about 0.3 weight parts flavor package is added to the buffered isomalt mixture. After mixing the resulting formulation, the formulation can be poured into a mold and cooled.

In some embodiments, one or more additional sweeteners are added to the compositions of the present invention. The one or more additional sweeteners can comprise any natural or artificial sweetener, including, but not limited to, sugar or any of the sugar substitutes described previously. In certain embodiments, the sweetener can include, glycyrrhizin, glycerol, inulin, lactitol, mabinlin, maltitol, mannitol, miraculin, monatin, monellin, osladin, pentadin, polydextrose, sorbitol, stevia, tagatose, thaumatin, acesulfame potassium, alitame, aspartame, cyclamate, dulcin, glucin, neotame, saccharin, sucralose, and combinations thereof. In certain embodiments, the sweetener comprises sucralose (1,6-Dichloro-1,6-dideoxy-β-D-fructofuranosyl-4-chloro-4-deoxy-α-D-galactopyranoside). The amount of sweetener added can vary, but is typically that amount required for a sufficiently "sweet" taste. For example, sweetener can be added to make the sweetness of the smokeless tobacco product comparable to that of sugar. In particular embodiments, sucralose is added in an amount of about 0.01% to about 2% by weight of the mixture, often in an amount of about 1% by weight of the mixture.

Various natural and/or artificial flavorants can also be added to the smokeless tobacco products of the present invention, and the character of these flavors can be described as, without limitation, fresh, sweet, herbal, confectionary, floral, fruity or spicy. Specific types of flavors include, but are not limited to, vanilla (e.g., vanillin optionally in complexed form), coffee, chocolate, cream, mint, spearmint, menthol, peppermint, wintergreen, lavender, cardamon, nutmeg, cinnamon, clove, cascarilla, sandalwood, honey, jasmine, ginger, anise, sage, licorice, lemon, orange, apple, peach, lime, cherry, and strawberry. See also, Leffingwill et al., Tobacco Flavoring for Smoking Products, R. J. Reynolds Tobacco Company (1972), which is incorporated herein by reference. Flavorings also can include components that are considered moistening, cooling or smoothening agents, such as eucalyptus. Flavorings can also include sensates, which can add a range of tactile, organoleptic properties to the smokeless tobacco products. For example, sensates can provide a warming, cooling, or tingling sensation. These flavors may be provided neat (i.e., alone) or in a composite (e.g., spearmint and menthol, or orange and cinnamon). Flavorants of this type can be present in an amount of from about 0.1% to about 15%, often between about 0.2% and about 1.5% by weight of the product mixture. In other embodiments, flavorants of this type can be present in an amount of from about 0.02% to about 15%, e.g., from about 0.05% to about 10% by weight of the product mixture. In certain embodiments, the flavorant is present in any amount of at least about 0.1% by weight or at least about 0.2% by weight of the mixture.

In certain embodiments, one or more substances are added to the smokeless tobacco composition for the purpose of soothing throat irritation that may develop during use of the product. The throat irritation mitigant can include any substance capable of mitigating or soothing irritation caused by the smokeless tobacco product, and expressly includes counter-irritants, anesthetics, and demulcents. Examples of throat irritation mitigants include sodium citrate, honey, ginger, pectin, capsaicin, camphor, dextromethorphan, echinacea, zinc gluconate, peppermint oil, spearmint oil, eucalyptus oil, glycerin, organic acids (e.g., citric acid, lactic acid, levulinic acid, or succinic acid), and combinations or extracts thereof (e.g., oleoresin ginger). Organic acids function by shifting the pH of the product into the acidic range, such as the pH range of about 3 to about 6.5. Typically, the organic acid is an organic acid containing at least one carboxylic acid group (e.g., carboxylic acids, dicarboxylic acids, and tricarboxylic acids). The amount of throat irritation mitigant used in the product can vary, but will be an amount sufficient to provide some degree of relief for throat irritation (e.g., a decrease in scratchy, lumpy sensations in the throat, a decrease in pain upon swallowing, a decrease in hoarseness while speaking, or a decrease in coughing). In exemplary embodiments, the throat irritation mitigant is present in an amount of at least about 1 weight percent, or at least about 2 weight percent, or at least about 3 weight percent (e.g., about 1 to about 10 weight percent).

Various other substances can be added to the compositions of the present invention. For example, excipients such as fillers or carriers for active ingredients (e.g., calcium polycarbophil, microcrystalline cellulose, hydroxypropylcellulose, sodium carboxymethylcellulose, cornstarch, silicon dioxide, calcium carbonate, lactose, and starches including potato starch, maize starch, etc.), thickeners, film formers and binders (e.g., hydroxypropyl cellulose, hydroxypropyl methylcellulose, acacia, sodium alginate, xanthan gum and gelatin), antiadherents (e.g., talc), glidants (e.g., colloidal silica), humectants (e.g., glycerin), preservatives and antioxidants (e.g., sodium benzoate and ascorbyl palmitate), surfactants (e.g., polysorbate 80), dyes or pigments (e.g., titanium dioxide or D&C Yellow No. 10), and lubricants or processing aids (e.g., calcium stearate or magnesium stearate) are added to the compositions in certain embodiments.

It is well-known that nicotine is subject to oxidation and accordingly, it may be advantageous to incorporate one or more anti-oxidants, such as, e.g., ascorbyl palmitate and/or sodium ascorbate, in a composition according to the invention. The one or more anti-oxidants may be present in a concentration of from about 0.05% w/w to about 0.3% w/w, such as, e.g., from about 0.1% w/w to about 0.25% w/w or from about 0.15% w/w to about 0.2% w/w in the smokeless tobacco product mixture.

Certain products of the present invention also can have outer coatings (e.g., an outer coating can be composed of ingredients such as carnauba wax and/or pharmaceutically acceptable forms of shellacs, glazing compositions and surface polish agents). Application of a coating can be accomplished using techniques such as airless spraying, fluidized bed coating, use of a coating pan, or the like. Materials for use as a coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof. In some embodiments, the coating can be a glazing or anti-sticking substance such as, for example, CAPOL 570C, which is available from Capol GmbH (Elmshorn, Germany).

Representative compositions according to the present invention can have various types of formats and configurations, and as a result, the character, nature, behavior, consistency, shape, form, size and weight of the composition can vary. The shape of a representative composition can be generally spherical, cylindrical (e.g., ranging form the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, capsule, and caplet types of products. The size and weight of the composition can also vary; for example, in certain particular embodiments, each smokeless tobacco product unit has a weight of between about 1.5 g and about 2.5 g (e.g., between about 1.8 g and about 2.2 g, such as about 1.9 g). In some embodiments, such products can comprise a particular amount of nicotine, e.g., between about 0.5 mg and about 5 mg nicotine (e.g., between about 1 mg and about 3 mg, such as about 2 mg).

In some embodiments, more than one lozenge formulation can be contained within the same smokeless tobacco product. For example, one portion or component of a given product can comprise one type of formulation, whereas a second portion or component of that product can comprise a second type of formulation. In some embodiments, the formulations may be substantially similar, but may vary from each other by one or two ingredients. For example, a two-component smokeless tobacco product can be provided wherein one component comprises tobacco extract and one component lacks tobacco extract; wherein one component has different flavorants than the other component; wherein one component is buffered and the other component is unbuffered, or wherein one component has different ratios of ingredients than the other component. The ratios of the two components or portions of a multi-component product generally can be, e.g., about 1:20 to about 20:1, about 1:10 to about 10:1, or about 1:5 to about 5:1 by volume.

In one specific embodiment, a multi-component smokeless tobacco product is provided, comprising one component that is colored (i.e., to which a colorant has been added), and one component that is uncolored (i.e., which contains no added colorant). In some embodiments, a multi-component smokeless tobacco product is provided, comprising one component that is colored (i.e., to which a colorant such as a dye or pigment has been added), and one component that is differently colored (i.e., having an entirely different color/hue or having a lighter shade, tint or brightness of the same color). Colorant as used herein is intended to cover any substance capable of modifying the color of the material and includes, but is not limited to, dyes and pigments.

Various colorants are known and can be incorporated in one or more components of the smokeless tobacco products described herein. Generally, water-soluble colorants are used in the smokeless tobacco products. They can be provided and incorporated into the smokeless tobacco products in liquid, powder, gel, or paste forms. Such colorants are preferably marketed as food-grade colorants. Certain colorants are synthetically derived ("artificial") and include, but are not limited to, FD&C Certified Dyes in various colors (e.g., red, orange, yellow, green, blue, brown, and black with certain specific dyes including, but not limited to, FD&C Yellow No. 5, FD&C Yellow No. 6, FD&C Blue No. 1, FD&C Blue No. 2, FD&C Red No. 3, FD&C Red No. 40, FD&C Green No. 3, Erythrosine, Fast Green FCF, Ponceau 4R, Allura Red, Red 2G, Fast Red E, Carmoisine, Amaranth, Chocolate Brown HT, Quinoline Yellow, Tartrazine, Sunset Yellow, Brilliant Blue FCF, Patent Blue V, Indigo Carmine, Brown HT, Black PN, Green S, and blends thereof, including Egg Yellow, Kesari B, Apple Green, Pea Green, Raspberry Red, Strawberry Red, Chocolate Brown Y, Chocolate Brown K1, Chocolate Brown FCF, Black CTB, Black NCTB, Black 1011, and mixtures thereof). Certain colorants are natural colorants and include, but are not limited to, caramel color/malt color, iron oxides, titanium dioxide, calcium carbonate, and color provided by such materials as red cabbage, paprika, safflower, elderberries, spinach, carrot, radish, purple sweet potato, black carrot, beets, turmeric, riboflavin, lutein, beta carotene/carotenoids, saffron, lycopene, chlorophyll, annatto, and mixtures thereof.

Although the present disclosure focuses on two-component products, it is noted that additional colored and/or uncolored components can be included (e.g., a three-component, four-component, or five-component product).

In certain embodiments, such multi-component smokeless tobacco products can be described as having two or more portions that are visually distinguishable by color. This can mean, for example, that the two or more portions exhibit different colors as determined by visual inspection by an unaided human eye in standard lighting conditions. Such smokeless tobacco products have two or more distinct regions that are visibly distinct in appearance and readily distinguishable from one another. Typically, such products comprise two or more portions wherein a given color is isolated within a particular geometric configuration (e.g., a spherical ball or "dot," column, or irregularly shaped configuration). For example, in certain specific embodiments, one portion is clear and one portion is green; one portion is clear and one portion is amber; one portion is clear and one portion is blue, etc. In certain specific embodiments, one portion is dark green and one portion is light green; one portion is dark amber and one portion is light amber; one portion is dark blue and the other portion is light blue, etc.

Figure 2:
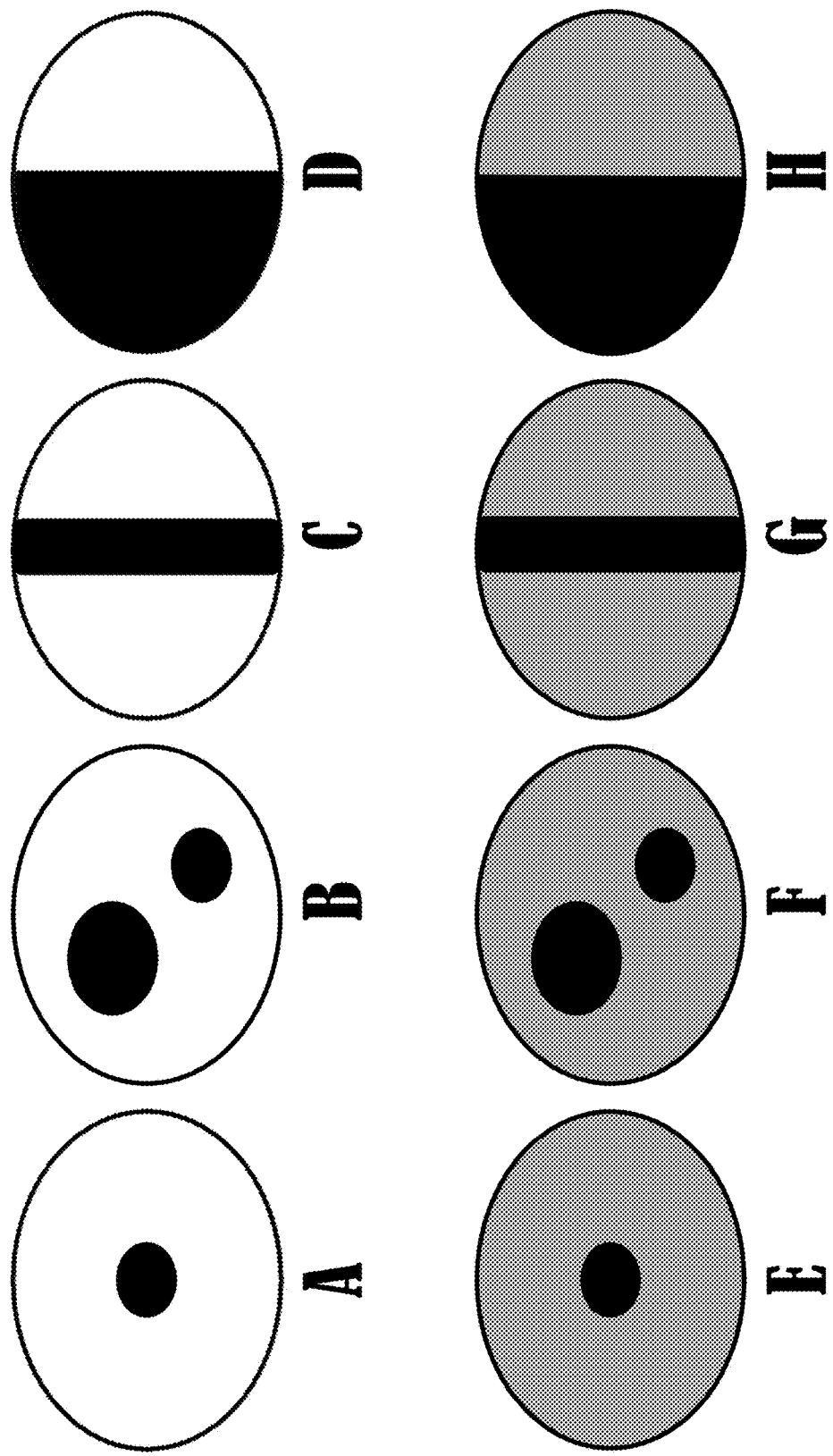
FIG. 2A-2H graphically illustrate various multi-component smokeless tobacco products provided according to the present disclosure.

In further embodiments, one portion is green and one portion is blue; one portion is green and one portion is amber; one portion is blue and one portion is amber, etc. In still further embodiments, the difference in color can be provided by a difference in translucency, e.g., wherein one portion is clear and one portion is translucent.

Where a discrete section of the smokeless tobacco product is colored, that discrete section can be, e.g., completely contained within an uncolored (or differently colored) section of the smokeless tobacco product (e.g., as a colored spherical portion or "dot" within an otherwise uncolored (or differently colored) material). See, for example, the embodiments illustrated in FIGS. 2A and 2E (single dot within colored and differently colored materials) and FIGS. 2B and 2F (two dots within colored and differently colored materials). Of course, such "dots" need not be spherical and can be, e.g., oval or irregularly shaped. Although in the illustrated embodiments, the dots are present in the interior (i.e., completely encased within the uncolored (or differently colored) component), in some embodiments, the dot can be located within the product such that at least a portion of the dot is exposed on the surface of the smokeless tobacco product.

In some embodiments, the discrete colored section may comprise a column-type configuration, running from one edge of the smokeless tobacco product to the other end. See, for example, the embodiments illustrated in FIGS. 2C and 2G (column within colored and differently colored material). In other embodiments, a larger portion of the discrete colored section can be exposed on the surface of the smokeless tobacco product (e.g., as a colored half, side by side with an uncolored (or differently colored) half of the smokeless tobacco product). See, for example, the embodiments illustrated in FIGS. 2D and 2H. It is also noted that the colored and uncolored portions (or colored and differently colored portions) illustrated in FIG. 2 can be switched. For example, in the embodiments of FIGS. 2A, 2B, 2E, and 2F, the dots could be colorless or lighter in color as compared with the exterior component. Similarly, in the embodiments of FIGS. 1C and 1G, the column could be colorless or lighter in color and the exterior component could be the colored portion. Of course, many more geometric configurations comprising a colored portion and an uncolored portion and/or a colored portion and a differently colored portion can be envisaged by one of skill in the art.

The percentage of colored section within the smokeless tobacco product can vary. For example, where the discrete colored section is completely contained within an uncolored (or differently colored) section of the smokeless tobacco product, the discrete colored section can comprise, for example, between about 5% and about 30% of the smokeless tobacco product by weight. Where the discrete colored section comprises a larger portion of the product (e.g., as a colored portion in a side-by-side type structure or as a column running from one side of the product to the other side of the product), the discrete colored section can comprise between about 10% and about 90% of the smokeless tobacco product by weight (e.g., between about 20% and about 80% of the smokeless tobacco product).

Where a discrete section of the smokeless tobacco product is colored, the colored section can be otherwise identical in composition to the uncolored (or differently colored) section or it may vary in composition (e.g., it may have different types or amounts of flavorings than the uncolored (or differently colored) section). Both the colored and uncolored (or differently colored) sections can, in some embodiments, comprise treated tobacco extract; however, in some embodiments, one or more sections within the smokeless tobacco product can comprise a different amount of treated tobacco extract than another section (e.g., one or more sections may comprise no treated tobacco extract).

The manners and methods used to formulate and manufacture the smokeless tobacco product can vary. For example, the compositions can be prepared via any method commonly used for the preparation of hard boiled confections. Exemplary methods for the preparation of hard confections can be found, for example, in LFRA Ingredients Handbook, Sweeteners, Janet M. Dalzell, Ed., Leatherhead Food RA (December 1996), pp. 21-44, which is incorporated herein by reference.

Typically, a first mixture of ingredients is prepared. The composition of the first mixture of ingredients can vary; however, it typically comprises a sugar substitute and may contain various additional substances (e.g., the sugar alcohol syrup, NaCl, preservatives, further sweeteners, water, and/or flavorings). In certain embodiments, it comprises the sugar substitute, salt, and vanillin. In other embodiments, the first mixture comprises the sugar substitute and the sugar alcohol syrup. Typically, the first mixture of ingredients does not contain the treated tobacco extract or other tobacco material.

The first mixture of ingredients is heated until it melts; subsequently, the mixture is heated to or past the hard crack stage. In confectionary making, the hard crack stage is defined as the temperature at which threads of the heated mixture (obtained by pulling a sample of cooled syrup between the thumb and forefinger) are brittle or as the temperature at which trying to mold the syrup results in cracking. According to the present method, the temperature at which the hard crack stage is achieved can vary, depending on the specific makeup of the product mixture but generally is between about 145° C. and about 170° C. Typically, the mixture is not heated above about 171° C., which is the temperature at which caramelization begins to occur. In the processes of the present invention, the mixture is typically heated to the hard crack stage temperature or above and then allowed to cool. The heating can be conducted at atmospheric pressure or under vacuum. Typically, the method of the present invention is conducted at atmospheric pressure.

In one exemplary embodiment, the first mixture of ingredients comprises a high percentage of isomalt and the mixture is heated to about 143° C. Once all components are dissolved, the temperature is raised past the hard crack stage (e.g., to about 166° C.). The mixture is heated to this temperature and then removed from the heat to allow the mixture to cool.

In certain embodiments, the treated tobacco extract and, optionally, additional components (e.g., additional tobacco materials, sweeteners, fillers, flavorants, and water) as described above are separately combined. The treated tobacco extract-containing mixture is added to the first mixture of ingredients, typically after the first mixture of ingredients has been removed from the heat. The addition of the treated tobacco extract-containing mixture may, in some embodiments, occur only after the heated first mixture of ingredients has cooled to a predetermined temperature (e.g., in certain embodiments, to about 132° C.). In certain embodiments, one or more flavorants are added to the treated tobacco extract-containing mixture immediately prior to adding the mixture to the first, heated mixture of ingredients. Certain flavorants are volatile and are thus preferably added after the mixture has cooled somewhat.

The combined mixture is then formed into the desired shape. In certain embodiments, the mixture is poured directly into molds, formed (e.g., rolled or pressed) into the desired shape, or extruded. If desired, the mixture can be extruded or injection molded. In certain embodiments, the mixture is formed or extruded into a mold of desired shape in an enclosed system, which may require decreased temperature and which may limit evaporation of certain mixture components. For example, such a system may limit the evaporation of volatile components including, but not limited to, flavorants. Other methods of producing smokeless tobacco products and/or lozenges are also intended to be encompassed herein.

Multi-component smokeless tobacco products can be produced according to the methods described herein. In some embodiments, the colored and the uncolored (or differently colored) materials can be co-deposited at the same time (i.e., using a "single pass" system). In some embodiments, the colored and the uncolored (or differently colored) materials can be deposited in different stages. For example, to prepare a smokeless tobacco product comprising a colored "dot" within an uncolored (or differently colored) matrix, the "dot" composition can be deposited first and then the uncolored or differently colored matrix composition can be subsequently deposited (i.e., using a "two pass" system).

Although the foregoing description has focused on treated tobacco extract-containing smokeless tobacco products, it is noted that the compositions and methods are intended to encompass other tobacco-derived or non-tobacco derived smokeless tobacco products as well. For example, tobacco-derived or non-tobacco derived nicotine or a derivative thereof can be used in the present invention. Representative nicotine-containing extracts can be provided using the techniques set forth in U.S. Pat. No. 5,159,942 to Brinkley et al., which is incorporated herein by reference. Extracts containing relatively high nicotine content can be buffered, e.g., using buffering agents such as citric acid to lower the pH of the extracts. Reference to a tobacco extract (e.g., ultrafiltered or translucent tobacco extracts) herein is intended to encompass any tobacco-derived extract of varying purity with respect to components found in tobacco, including highly purified nicotine-containing extracts produced from tobacco material.

As mentioned above, nicotine may be present in any suitable form. Normally, nicotine is selected from the group consisting of nicotine base, nicotine hydrochloride, nicotine dihydrochloride, nicotine monotartrate, nicotine bitartrate, nicotine sulfate, nicotine zinc chloride such as nicotine zinc chloride monohydrate and nicotine salicylate. In some embodiments, nicotine is in its free base form, which can optionally be sorbed on a carrier (e.g., microcrystalline cellulose) for inclusion in a smokeless tobacco product. See, for example, the nicotine/carrier compositions set forth in US Pat. Pub. No. 2004/0191322 to Hansson, which is incorporated by reference herein.

Typical conditions associated with manufacture of food grade products such as described herein include control of heat and temperature (i.e., the degree of heat to which the various ingredients are exposed during manufacture and the temperature of the manufacturing environment), moisture content (e.g., the degree of moisture present within individual ingredients and within the final composition), humidity within the manufacturing environment, atmospheric control (e.g., nitrogen atmosphere), airflow experienced by the various ingredients during the manufacturing process, and other similar types of factors. Additionally, various process steps involved in product manufacture can involve selection of certain solvents and processing aids, use of heat and radiation, refrigeration and cryogenic conditions, ingredient mixing rates, and the like. The manufacturing conditions also can be controlled due to selection of the form of various ingredients (e.g., solid, liquid, or gas), particle size or crystalline nature of ingredients of solid form, concentration of ingredients in liquid form, or the like. Ingredients can be processed into the desired composition by techniques such as extrusion, compression, spraying, and the like.

In certain embodiments, the smokeless tobacco product is transparent or translucent as defined herein. Transparency/translucency can be determined by any means commonly used in the art; however, it is commonly measured by spectrophotometric light transmission over a range of wavelengths (e.g., from about 400-700 nm). Transmission measurements for the smokeless tobacco products of the present invention are typically higher than those of traditional tobacco-extract containing smokeless tobacco products. Translucency can also be confirmed by visual inspection by simply holding the smokeless tobacco product up to a light source and determining if light travels through the product in a diffuse manner.

Aspects of the present invention are more fully illustrated by the following examples, which are set forth to illustrate certain aspects of the present invention and are not to be construed as limiting thereof.

EXPERIMENTAL

Example 1

Ultrafiltration of Tobacco Extract

A tobacco extract is prepared by mixing hot water (140-155° C.) and tobacco at a ratio of 8:1 water:tobacco. The mixture is agitated for 1 hour and is then centrifuged. The supernatant thus obtained is evaporated to ~25% solids. The extract is centrifuged again (4000 rpm for 10 min) in 50 mL conical tubes to remove any large particles that remain. The supernatant is filtered using a vacuum filter system and 7 μm filter paper.

The filtered supernatant is diluted 1:1 with distilled, deionized water and placed in the reservoir of a Millipore Tangential Flow Filter (TFF) system. A first TFF system was fitted with a Pellicon Biomax-50 (MWCO 50,000 Da) cartridge. A second TFF system was fitted with a Pellicon Biomax-5 (MWCO 5,000 Da) cartridge. The permeate passing through the first TFF system is directed into the reservoir of the second TFF system. The resulting final permeate is collected in a clean beaker. This ultrafiltered extract is placed in a freezer at −80° C. overnight, and then removed and placed in a freeze dryer. The tray of the freeze dryer was set to −20° C. and the vacuum was set at 0.600 mBar. The extract is kept in the freeze dryer until dry, approximately 36-48 hours.

Beginning with 600 mL of evaporated tobacco extract (~25% solids), 50 g of freeze-dried material was obtained. Assuming 60% of the water was evaporated from the initial tobacco material, the extract represented 1500 mL (1500 g) of water that was exposed to 187.5 g tobacco (8:1 water:tobacco ratio). Of that mass, 45% (84.4 g) is hot water extractable. Of the hot water extractable material, 59% passed through the ultrafiltration freeze-drying process (i.e., 26.6% of the starting tobacco mass made it through the ultrafiltration freeze-drying process).

The ultrafiltered, freeze-dried extract has the consistency of light brown sugar, is highly hygroscopic, and has a pleasant/sweet aroma. Analysis shows that the extract contains sugars, organic acids, salts, alkaloids, and nicotine. In humid conditions, it forms a brown, viscous, translucent syrup. The ultrafiltered, freeze-dried extract has much less color and more clarity than the initial tobacco extract.

Example 2

Preparation of Smokeless Tobacco Product (with No Heat Treatment)

Isomalt, NaCl, and vanillin are mixed in a pot and the temperature of the mixture is brought to 143° C. The mixture is held at 143° C. until the isomalt is melted and the temperature is then increased to 166° C. In a separate vessel, treated tobacco extract from Example 1, maltitol syrup, $H_2O$, sucralose, and, optionally, L-lysine are mixed to forth a solution. Optionally, in a second separate vessel, water and sodium hydroxide are mixed to form a solution.

The isomalt mixture is removed from the heat and allowed to cool to 132° C. The remaining components (i.e., the extract containing solution and optional sodium hydroxide solution) are combined and, optionally, one or more flavorings are added to the combined solution. The combined solution is poured into the hot isomalt mixture and folded in.

The resulting mixture is poured into molds to form smokeless tobacco products. When the mixture becomes too viscous to pour, the mixture can be heated in a microwave using high heat (e.g., for about 7 seconds). Representative smokeless tobacco product mixtures are set forth below. Mixture 1 below contains no base, while Mixtures 2 and 3 contain sodium hydroxide at varying levels.

| MIXTURE 1 | |
|---|---|
| Ingredient | Percent by weight |
| Isomalt ST-M* | 90.37 |
| Maltitol syrup | 1.00 |
| Ultrafiltered tobacco extract (77% solids) | 3.84 |
| NaCl | 1.00 |
| Vanillin | 0.30 |
| Sucralose | 0.20 |
| $H_2O$ | 3.16 |
| Flavorant | 0.13 |
| Final pH = 4.5 | |

*Isomalt in which 1,6-GPS and 1,1-GPM are present in essentially equimolar amounts and which has a medium grain size, the diameter of approximately 90% of all particles being <3 mm.

| MIXTURE 2 | |
|---|---|
| Ingredient | Percent by weight |
| Isomalt ST-M | 90.37 |
| Maltitol syrup | 1.00 |
| Ultrafiltered tobacco extract (77% solids) | 3.84 |
| NaCl | 1.00 |
| Vanillin | 0.30 |
| Sucralose | 0.20 |
| $H_2O$ | 3.01 |
| Flavorant | 0.13 |
| NaOH | 0.15 |
| Final pH = 6.6 | |

| MIXTURE 3 | |
|---|---|
| Ingredient | Percent by weight |
| Isomalt ST-M | 90.37 |
| Maltitol syrup | 1.00 |
| Ultrafiltered tobacco extract (77% solids) | 3.84 |
| NaCl | 1.00 |
| Vanillin | 0.30 |
| Sucralose | 0.20 |
| H₂O | 2.86 |
| Flavorant | 0.13 |
| NaOH | 0.30 |
| Final pH = 8.1 | |

Example 3

Preparation of Smokeless Tobacco Product (with Heat-Treated Tobacco Extract)

Certain smokeless tobacco products are prepared using tobacco extract that has been heat treated with different additives to reduce the amount of acrylamide. A heat-treated tobacco extract is prepared by combining an ultrafiltered tobacco extract prepared according to Example 1 with an additive to reduce acrylamide in water and stirring until a solution is formed. The resulting mixture is heated to 88° C. and held at this temperature for 60 minutes. The mixture is cooled and additional water is added to return the mixture to the starting weight of 200 g.

Mixtures 4-7, described in the tables below, relate to smokeless tobacco products comprising heat-treated tobacco extract prepared in this way. Part A outlines the components of the heat treatment process. The mixtures comprise different additives for the reduction of acrylamide. The resulting heat-treated tobacco extract can be stored frozen until use. This heat-treated tobacco extract is used in the preparation of a smokeless tobacco product according to the method provided above, using the components detailed in Part B of Mixtures 4-7.

As one specific example, heat-treated tobacco extract is prepared by combining H₂O (65.79 g), treated tobacco extract, 77% solids (118.42 g), NaOH (8.90 g), and L-lysine (6.89 g), stirring until dissolved, heating to 88° C., and holding at this temperature for 60 minutes. The mixture is cooled to 29° C. and additional H₂O is added to return the mixture to the starting weight of 200 g.

| MIXTURE 4 | |
|---|---|
| Part A - Extract Treatment with NaOH and L-lysine | |
| Ingredient | Grams |
| Ultrafiltered tobacco extract (77% solids) | 118.42 |
| H₂O | 65.79 |
| NaOH | 8.50 |
| L-lysine | 7.29 |
| Part B - Preparation of Smokeless Tobacco Product | |
| Ingredient | Percent by weight |
| Isomalt ST-M | 90.00 |
| Maltitol syrup | 1.00 |
| Heat-treated tobacco extract | 7.60 |
| NaCl | 1.00 |
| Vanillin | 0.10 |
| Sucralose | 0.15 |
| Flavorant | 0.15 |
| Final pH = 7.76 | |

| MIXTURE 5 | |
|---|---|
| Part A - Extract Treatment with NaOH and L-cysteine 97% | |
| Ingredient | Grams |
| Ultrafiltered tobacco extract (77% solids) | 118.42 |
| H₂O | 65.79 |
| NaOH | 8.50 |
| L-cysteine 97% | 7.29 |
| Part B - Preparation of Smokeless Tobacco Product | |
| Ingredient | Percent by weight |
| Isomalt ST-M | 90.00 |
| Maltitol syrup | 1.00 |
| Heat-treated tobacco extract | 7.60 |
| NaCl | 1.00 |
| Vanillin | 0.10 |
| Sucralose | 0.15 |
| Flavorant | 0.15 |
| Final pH = 7.86 | |

| MIXTURE 6 | |
|---|---|
| Part A - Extract Treatment with NaOH and Asparaginase | |
| Ingredient | Grams |
| Ultrafiltered tobacco extract (77% solids) | 118.42 |
| H₂O | 65.79 |
| NaOH | 8.50 |
| Asparaginase | 1.50 |
| Part B - Preparation of Smokeless Tobacco Product | |
| Ingredient | Percent by weight |
| Isomalt ST-M | 90.00 |
| Maltitol syrup | 1.00 |
| Heat-treated tobacco extract | 7.60 |
| NaCl | 1.00 |
| Vanillin | 0.10 |
| Sucralose | 0.15 |
| Flavorant | 0.15 |
| Final pH = 8.29 | |

MIXTURE 7

Part A - Extract Treatment with NaOH and
3% Hydrogen Peroxide

| Ingredient | Grams |
|---|---|
| Ultrafiltered tobacco extract (77% solids) | 118.42 |
| NaOH 50% solution | 17.00 |
| 3% hydrogen peroxide solution | 80.00 |

Part B - Preparation of Smokeless Tobacco Product

| Ingredient | Percent by weight |
|---|---|
| Isomalt ST-M | 90.00 |
| Maltitol syrup | 1.00 |
| Heat-treated tobacco extract | 7.60 |
| NaCl | 1.00 |
| Vanillin | 0.10 |
| Sucralose | 0.15 |
| Flavorant | 0.15 |
| Final pH = 8.10 | |

The compositions comprising heat-treated tobacco extract exhibited relatively low acrylamide levels in the final smokeless tobacco products (Mixture 4=343 ng/g, Mixture 5=44.8 ng/g, Mixture 6=190 ng/g, and Mixture 7=445 ng/g). These acrylamide levels represent a significant decrease as compared with tobacco extract that has not been heat treated. For example, heat treated tobacco extract can exhibit up to about a 98% reduction in acrylamide level over non-heat-treated tobacco extract. The values for smokeless tobacco products represented by Mixtures 4-7 represent a reduction in acrylamide level of from about 60% to about 96% over a comparable smokeless tobacco product wherein the tobacco extract has not been heat treated.

Example 4

Preparation of Smokeless Tobacco Product Combining Tobacco Extract and Particulate Tobacco Isomalt and maltitol syrup are mixed in a pot until the isomalt is melted. In a separate vessel, treated tobacco extract prepared according to Example 1, H$_2$O, NaCl, sucralose, and flavorings are mixed to form a solution.

The isomalt mixture is removed from the heat and allowed to cool. The extract-containing solution is poured into the hot isomalt mixture and folded in. Optionally, milled tobacco is added, either to the isomalt mixture (prior to combining the isomalt mixture with the extract-containing solution, or to the combined mixture).

The resulting combined mixture is poured into molds to form smokeless tobacco products. When the mixture becomes too viscous to pour, the mixture can be heated in a microwave using high heat (e.g., for about 7 seconds). Representative smokeless tobacco product mixtures are set forth below as Mixtures 8-10.

MIXTURE 8

| Ingredient | Percent by weight |
|---|---|
| Isomalt ST-M | 92.16 |
| Maltitol syrup | 1.00 |
| Ultrafiltered tobacco extract (77% solids) | 2.00 |
| NaCl | 0.70 |

-continued

MIXTURE 8

| Ingredient | Percent by weight |
|---|---|
| Sucralose | 0.04 |
| H$_2$O | 4.00 |
| Flavorant | 0.10 |

MIXTURE 9

| Ingredient | Percent by weight |
|---|---|
| Isomalt ST-M | 87.55 |
| Maltitol syrup | 0.95 |
| Ultrafiltered tobacco extract (77% solids) | 1.9 |
| NaCl | 0.66 |
| Sucralose | 0.04 |
| H$_2$O | 3.8 |
| Flavorant | 0.10 |
| Milled tobacco | 5.0 |

MIXTURE 10

| Ingredient | Percent by weight |
|---|---|
| Isomalt ST-M | 91.24 |
| Maltitol syrup | 0.99 |
| Ultrafiltered tobacco extract (77% solids) | 0.69 |
| NaCl | 3.96 |
| Sucralose | 0.04 |
| H$_2$O | 3.96 |
| Flavorant | 0.10 |
| Milled tobacco | 1.0 |

Example 5

Preparation of Smokeless Tobacco Product Comprising Throat Irritation Mitigant a) Ginger as Throat Irritation Mitigant Panelists are provided with a lozenge comprising 3% by weight tobacco extract and 1.5% by weight ginger powder and a control lozenge comprising 3% by weight tobacco extract (without ginger). The control lozenge is sampled first, followed by the ginger-containing lozenge. Using a rating scale of 1-15, users note some degree of throat irritation associated with the control lozenge. Users note a decrease in both peak mouth sensation intensity and peak throat sensation intensity and note an overall preference for the ginger-containing lozenge.

b) Sodium Citrate and Oleoresin Ginger as Throat Irritation Mitigant

Panelists are provided with a lozenge comprising 3% by weight tobacco extract with 2% by weight sodium citrate and 0.35% by weight oleoresin ginger and a control lozenge comprising 3% by weight tobacco extract (without sodium citrate or oleoresin ginger). The oleoresin ginger and sodium citrate-containing lozenge is sampled first, followed by the control lozenge. Using a rating scale of 1-15, users note an increase in both peak mouth sensation intensity and peak throat sensation intensity for the oleoresin ginger and sodium citrate-containing lozenge. Because the oleoresin ginger and sodium citrate-containing lozenge was sampled first, this result may be due to an inability of the panelists to distinguish the differences between the samples. It is also possible that the oleoresin ginger, which inherently has a strong peppery sensation as well as an intense ginger flavor, successfully masks any throat irritation caused by other components of the lozenge, but may itself contribute to throat irritation at certain inclusion levels.

Example 6

Alternative Processing of Tobacco Extract with TSNA Removal

A tobacco extract is prepared as described in Example 1, except instead of freeze drying, the liquid, ultrafiltered extract is passed through a non-imprinted polymer (NIP) cartridge available from Biotage LLC, Charlotte, N.C. to remove tobacco specific nitrosamines (TSNAs). Surprisingly, it is found that the NIP cartridge removes even more of the brown tobacco pigments remaining in the ultrafiltered extract, resulting in a significant increase in light transmission through the extract. The resulting treated extract is concentrated to about 20% solids and spray dried.

FIG. 1 shows the visible light transmission spectrum of the treated tobacco extract processed according to this example to demonstrate color removal. A Hewlett Packard 8463 UV/Visible Spectrometer equipped with both tungsten and deuterium lamps is used to gather the data. Samples are measured neat (as-is) using a 1 cm path-length quartz cell. Water is used as a reference for 100% transmittance.

As illustrated, each step in the process resulted in higher levels of transmittance for much of the visible light spectrum, which confirms that the process of the invention increases translucence of the extract and, by extension, translucence of products made using the extract. For a wavelength of 600 nm (yellow to orange light), the amount of light transmitted approximately doubles after each step, going from ~10% (extract prior to ultrafiltration) to ~20% (after 50 kDa ultrafiltration) to ~40% (after 5 kDa ultrafiltration) to ~80% (after NIP cartridge).

Example 7

Alternative Processing of Tobacco Extract to Inhibit Acrylamide Formation

The process of Example 1 is altered by adding 0.1 to about 0.5% by weight of asparaginase (available as PreventASe™ from DSM Food Specialties, Heerlen, N L or Acrylaway® from Novozymes, A/S, Bagsvaerd, DK) to the 8:1 water:tobacco slurry of Example 1 and maintaining the temperature of the slurry at no more than about 60° C. or heating the slurry as indicated in Example 1 and thereafter cooling the slurry to no more than about 60° C. before addition of the asparaginase. Following the enzyme treatment, the enzyme is optionally deactivated by raising the temperature of the slurry to at least about 70° C. for 30 minutes or more.

The filtration steps of Example 1 are then performed. The ultrafiltration treatment steps remove the asparaginase since asparaginase has a molecular weight of about 50 kDa. The extract is then concentrated, such as by simple evaporation through heating, treatment in a rotary evaporator under vacuum, reverse osmosis, or use of a thin-film evaporator.

Example 8

Preparation of One-Component Smokeless Tobacco Product

A: Preparation of Smokeless Tobacco Product

Isomalt, maltitol syrup, and vanillin are combined to form a slurry. Separately, NaCl is mixed with water, and the resulting NaCl solution is added to the slurry in a cooking vessel. The temperature of the isomalt mixture in the cooking vessel is brought to 350° F. (about 177° C.). In a separate vessel, the nicotine solution, vanillin, sucralose, citric acid, sucralose, additional flavoring(s) and colorant(s) are mixed.

The isomalt mixture is allowed to cool to 300° F. (about 149° C.). The nicotine solution-containing mixture is added to the hot isomalt mixture and stirred for about 20 seconds or until well-blended. The resulting mixture is removed from the heat and transferred to a depositor. From the depositor, the resulting mixture is deposited into molds to form smokeless tobacco products (each product designed as a 1.0 gram weight/piece with approximately 2 mg nicotine). The smokeless tobacco products are allowed to cool and set and then dispensed from the molds. A representative product mixture is set forth below.

| PRODUCT MIXTURE | |
|---|---|
| Ingredient | Percent by weight |
| Isomalt ST-M | 95.965 |
| Maltitol syrup | 1.00 |
| Tobacco extract* | 1.40 |
| NaCl | 1.40 |
| Vanillin | 0.05 |
| Sucralose | 0.01 |
| Citric acid | 0.05 |
| $H_2O$ | 5.00 |
| Flavorant | 0.05 |
| Colorant | 0.075 |

*The tobacco extract is in the form of a nicotine solution comprising 7.5% nicotine and 93.5% water.

B: Coating of Smokeless Tobacco Product

Optionally, a coating can be applied to the smokeless tobacco product. CAPOL 570C, which is available from Capol GmbH (Elmshorn, Germany) can be used as the coating material. The uncoated smokeless tobacco products are weighed and this weight is used to calculate the amount of CAPOL 570C to add. The uncoated products are stirred to evenly coat with the CAPOL 570C. An exemplary amount of coating added to the products is based on the following table.

| COATED PRODUCT | |
|---|---|
| Ingredient | Percent by weight |
| Uncoated smokeless tobacco product | 99.88 |
| CAPOL 570C | 0.20 |

Example 9

Preparation of Two-Component Smokeless Tobacco Product

A: Preparation of Amber Colored Core Component

Isomalt, maltitol syrup, and vanillin are combined to form a slurry. Separately, NaCl is mixed with water, and the resulting NaCl solution is added to the slurry in a cooking vessel. The temperature of the isomalt mixture in the cooking vessel is brought to 350° F. (about 177° C.). In a separate vessel, Nicotine solution, vanillin, sucralose, citric acid, sucralose, additional flavoring(s) and colorant(s) are mixed.

The isomalt mixture is allowed to cool to 300° F. (about 149° C.). The nicotine solution-containing mixture is added to the hot isomalt mixture and stirred for about 20 seconds or until well-blended. The resulting mixture is removed from the heat and transferred to a depositor. A representative amber colored core component mixture is set forth below.

| COLORED CORE COMPONENT MIXTURE | |
| --- | --- |
| Ingredient | Percent by weight |
| Isomalt ST-M | 95.14 |
| Maltitol syrup | 1.00 |
| Tobacco extract* | 1.40 |
| NaCl | 1.40 |
| Vanillin | 0.05 |
| Sucralose | 0.01 |
| Citric acid | 0.05 |
| $H_2O$ | 5.00 |
| Flavorant | 0.05 |
| Colorant | 0.90 |

*The tobacco extract is in the form of a nicotine solution comprising 7.5% nicotine and 93.5% water.

B: Preparation of Uncolored Outer Component

Isomalt, maltitol syrup, and vanillin are combined to form a slurry. Separately, NaCl is mixed with water, and the resulting NaCl solution is added to the slurry in a cooking vessel. The temperature of the isomalt mixture in the cooking vessel is brought to 350° F. (about 177° C.). In a separate vessel, nicotine solution, vanillin, sucralose, citric acid, sucralose, and additional flavoring(s) are mixed.

The isomalt mixture is allowed to cool to 300° F. (about 149° C.). The nicotine solution-containing mixture is added to the hot isomalt mixture and stirred for about 20 seconds or until well-blended. The resulting mixture is removed from the heat and transferred to a depositor. A representative uncolored outer component mixture is set forth below.

| UNCOLORED OUTER COMPONENT MIXTURE | |
| --- | --- |
| Ingredient | Percent by weight |
| Isomalt ST-M | 96.04 |
| Maltitol syrup | 1.00 |
| Tobacco extract* | 1.40 |
| NaCl | 1.40 |
| Vanillin | 0.05 |
| Sucralose | 0.01 |
| Citric acid | 0.05 |
| $H_2O$ | 5.00 |
| Flavorant | 0.05 |

*The tobacco extract is in the form of a nicotine solution comprising 7.5% nicotine and 93.5% water.

C: Construction of Smokeless Tobacco Product

The isomalt mixtures described in Sections A and B are dispensed from the depositor as follows, at a temperature that allows the mixtures to maintain some degree of flowability. From the depositor, the colored core component mixture is deposited into the molds first, followed by the uncolored outer component mixture. Either a one-pass or two-pass system can be used. In a one-pass system, both components are dispensed into a single mold before dispensing into additional molds. The colored core component mixture is deposited into the mold first, followed immediately by the uncolored outer component mixture. In a two-pass system, a depositor containing the colored core component mixture first deposits the colored mixture into a series of molds; subsequently, a depositor containing the uncolored outer component mixture deposits the uncolored mixture into the molds to form the products. The smokeless tobacco products are allowed to cool and set and then dispensed from the molds. Such smokeless tobacco products are characterized by an amber-colored "dot" exposed on the surface of the product.

D: Coating of Smokeless Tobacco Product

Optionally, a coating can be applied to the smokeless tobacco products described herein, as detailed in Example 8B. Exemplary amounts of coating added to the products are based on the following table.

| COATED TWO-COMPONENT PRODUCT | |
| --- | --- |
| Ingredient | Percent by weight |
| Uncoated smokeless tobacco product | 99.88 |
| CAPOL 570C | 0.20 |

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A smokeless tobacco product comprising:
    a. a first portion comprising at least about 80% by weight isomalt and a sugar alcohol syrup; and
    b. a second portion comprising at least about 80% by weight isomalt and a sugar alcohol syrup,
    wherein the two portions are visually distinguishable by color, and wherein at least one portion comprises a translucent tobacco extract, wherein the translucent tobacco extract is an ultrafiltered tobacco extract consisting of only compounds with molecular weight below about 5,000 Da.

2. The smokeless tobacco product of claim 1, wherein the first and second portions comprise different amounts of translucent tobacco extract.

3. The smokeless tobacco product of claim 1, wherein the first and second portions comprise different amounts of buffer.

4. The smokeless tobacco product of claim 1, wherein the first and second portions comprise flavorants of different types or different amounts.

5. The smokeless tobacco product of claim 1, wherein the second portion is completely encased within the first portion.

6. The smokeless tobacco product of claim 1, wherein both the first and second portions are exposed on the surface of the smokeless tobacco product.

7. The smokeless tobacco product of claim 1, wherein the ratio of the first portion to the second portion is between about 1:20 and about 20:1 by volume.

8. The smokeless tobacco product of claim 1, wherein the ratio of the first portion to the second portion is between about 1:10 and about 10:1 by volume.

9. The smokeless tobacco product of claim 1, wherein the first portion comprises no added colorants.

10. The smokeless tobacco product of claim 1, wherein the first and second portions comprise added colorants of different types or different amounts.

11. The smokeless tobacco product of claim 1, wherein:
the first portion comprises isomalt, maltitol syrup, sodium chloride, vanillin, sucralose, citric acid, a translucent tobacco extract, and flavorant; and
the second portion comprises isomalt, maltitol syrup, sodium chloride, vanillin, sucralose, citric acid, a translucent tobacco extract, flavorant, and a colorant.

12. The smokeless tobacco product of claim 1, wherein the smokeless tobacco product is in the form of a lozenge with a weight of between about 1.8 and about 2.2 g.

13. The smokeless tobacco product of claim 12, wherein the smokeless tobacco product comprises between about 0.5 mg and about 5 mg nicotine.

14. The smokeless tobacco product of claim 1, wherein the isomalt is present in an amount of at least about 90% by weight of the smokeless tobacco product.

15. The smokeless tobacco product of claim 1, wherein the isomalt is present in an amount of at least about 95% by weight of the smokeless tobacco product.

16. The smokeless tobacco product of claim 1, wherein one or both of the portions comprise one or more of the following:
a flavorant in an amount from about 0.05 to about 15 percent by weight of the smokeless tobacco product;
sucralose in the amount from about 0.01 to about 2 percent by weight of the smokeless tobacco product; and
sodium chloride in the amount from about 0.5 to about 10 percent by weight of the smokeless tobacco product.

17. The smokeless tobacco product of claim 1, further comprising a throat irritation mitigant.

18. The smokeless tobacco product of claim 1, further comprising a coating on at least a portion thereof.

19. The smokeless tobacco product of claim 1, wherein one or both of the first and second portions comprises a translucent tobacco extract in the form of an aqueous nicotine solution.

20. The smokeless tobacco product of claim 1, wherein the translucent tobacco extract comprises at least one sugar, at least one organic acid, at least one salt, and nicotine.

* * * * *